(12) United States Patent
Bikard et al.

(10) Patent No.: US 12,246,061 B2
(45) Date of Patent: *Mar. 11, 2025

(54) SEQUENCE SPECIFIC ANTIMICROBIALS

(71) Applicant: The Rockefeller University, New York, NY (US)

(72) Inventors: David Bikard, Paris (FR); Luciano Marraffini, Brooklyn, NY (US)

(73) Assignee: The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/425,204

(22) Filed: Jan. 29, 2024

(65) Prior Publication Data

US 2024/0165210 A1 May 23, 2024

Related U.S. Application Data

(60) Continuation of application No. 17/168,971, filed on Feb. 5, 2021, now Pat. No. 12,168,040, and a continuation of application No. 17/088,297, filed on Nov. 3, 2020, and a continuation of application No. 17/088,302, filed on Nov. 3, 2020, and a division of application No. 16/877,010, filed on May 18, 2020, said application No. 17/168,971 is a division of application No. 16/877,010, filed on May 18, 2020, and a division of application No. 16/877,030, filed on May 18, 2020, now Pat. No. 11,135,273, said application No. 17/088,302 is a division of application No. 16/877,030, filed on May 18, 2020, now Pat. No. 11,135,273, said application No. 17/088,297 is a division of application No. 16/877,030, filed on May 18, 2020, now Pat. No. 11,135,273, application No. 18/425,204 is a continuation of application No. 15/159,929, filed on May 20, 2016, now Pat. No. 11,918,631, said application No. 16/877,030 is a division of application No. 15/159,929, filed on May 20, 2016, now Pat. No. 11,918,631, said application No. 17/168,971 is a continuation of application No. 15/159,929, filed on May 20, 2016, now Pat. No. 11,918,631, said application No. 16/877,010 is a continuation of application No. 14/766,675, filed as application No. PCT/US2014/015252 on Feb. 7, 2014, now Pat. No. 10,660,943, said application No. 15/159,929 is a division of application No. 14/766,675, filed as application No. PCT/US2014/015252 on Feb. 7, 2014, now Pat. No. 10,660,943.

(60) Provisional application No. 61/761,971, filed on Feb. 7, 2013.

(51) Int. Cl.
*A61K 38/46* (2006.01)
*A01N 63/00* (2020.01)
*A61K 31/7105* (2006.01)
*A61K 31/713* (2006.01)
*A61K 45/06* (2006.01)
*C12N 9/16* (2006.01)
*C12N 9/22* (2006.01)
*C12N 15/113* (2010.01)
*C12N 15/74* (2006.01)

(52) U.S. Cl.
CPC ............ *A61K 38/465* (2013.01); *A01N 63/00* (2013.01); *A61K 31/7105* (2013.01); *A61K 31/713* (2013.01); *A61K 45/06* (2013.01); *C12N 9/16* (2013.01); *C12N 9/22* (2013.01); *C12N 15/113* (2013.01); *C12N 15/74* (2013.01); *C12Y 301/00* (2013.01); *C12N 2310/10* (2013.01); *C12N 2310/20* (2017.05); *C12N 2795/10331* (2013.01); *C12N 2795/10332* (2013.01); *C12N 2795/10343* (2013.01); *C12N 2795/10371* (2013.01)

(58) Field of Classification Search
None
See application file for complete search history.

(56) References Cited

U.S. PATENT DOCUMENTS

| | | |
|---|---|---|
| 8,071,352 B2 | 12/2011 | Yoon et al. |
| 9,822,372 B2 | 11/2017 | Zhang et al. |
| 10,463,049 B2 | 11/2019 | Clube et al. |

(Continued)

FOREIGN PATENT DOCUMENTS

| | | |
|---|---|---|
| EP | 2325332 B1 | 5/2011 |
| WO | 2012/164565 A1 | 12/2012 |
| WO | 2013/176772 A1 | 11/2013 |

OTHER PUBLICATIONS

Jiang, W., et al., RNA-Guided Editing of Bacterial Genomes Using CRISPR-Cas Systems, Nature Biotechnology, Jan. 29, 2013, vol. 31, pp. 233-241.

(Continued)

*Primary Examiner* — Nancy J Leith
(74) *Attorney, Agent, or Firm* — Hodgson Russ LLP

(57) ABSTRACT

Provided are compositions and methods for selectively reducing the amount of antibiotic resistant and/or virulent bacteria in a mixed bacteria population, or for reducing any other type of unwanted bacteria in a mixed bacteria population. The compositions and methods involve targeting bacteria that are differentiated from other members of the population by at least one unique clustered regularly interspaced short palindromic repeats (CRISPR) targeted DNA sequence. The compositions and methods can be readily adapted to target any bacteria or any bacteria plasmid, or both.

24 Claims, 7 Drawing Sheets

Specification includes a Sequence Listing.

(56) References Cited

U.S. PATENT DOCUMENTS

| | | | |
|---|---|---|---|
| 10,506,812 | B2 | 12/2019 | Clube |
| 10,524,477 | B2 | 1/2020 | Clube et al. |
| 10,660,943 | B2 | 5/2020 | Bikard et al. |
| 11,135,273 | B2 | 10/2021 | Bikard et al. |
| 11,452,765 | B2 | 9/2022 | Bikard et al. |
| 11,491,209 | B2 | 11/2022 | Bikard et al. |
| 11,491,210 | B2 | 11/2022 | Bikard et al. |
| 11,497,797 | B2 | 11/2022 | Bikard et al. |
| 11,918,631 | B2 * | 3/2024 | Bikard ............... A61K 31/7105 |
| 2003/0049841 | A1 | 3/2003 | Short |
| 2009/0155768 | A1 | 6/2009 | Scholl et al. |
| 2010/0076057 | A1 | 3/2010 | Sontheimer et al. |
| 2011/0002889 | A1 | 1/2011 | Barrangou et al. |
| 2014/0068797 | A1 | 3/2014 | Doudna et al. |
| 2016/0115489 | A1 | 4/2016 | Zhang et al. |
| 2017/0196225 | A1 | 7/2017 | Clube et al. |

OTHER PUBLICATIONS

Westwater, C., et al., Use of Genetically Engineered Phage to Deliver Antimicrobial Agents to Bacteria: An Alternative Therapy for Treatment of Bacterial Infections, Antimicrobial Agents and Chemotherapy, Apr. 2003, vol. 57, pp. 1301-1307.

Nakamura, S., et al., Metagenomic Diagnosis of Bacterial Infections, Emerging Infectious Diseases, Nov. 2008, vol. 14, pp. 1784-1786.

Bikard, D., et al., CRISPR Interference Can Prevent Natural Transformation and Virulence Acquisition during In Vivo Bacterial Infection, CellHost & Microbe, Aug. 15, 2012, vol. 12, 117-186.

Westwater, C., et al., Development of a P1 phagemid system for the delivery of DNA into Gram-negative bacteria, Microbiology, 2002, vol. 148, pp. 943-950.

Jinek, M., et al., A Programmable Dual-RNA-Guided DNA Endonuclease in Adaptive Bacterial Immunity, Science, Jun. 28, 2012, vol. 337, pp. 816-821.

Brouns, S.J.J., et al., Small CRISPR RNAs Guide Antiviral Defense in Prokaryotes, Science, Aug. 15, 2008, vol. 321, pp. 960-964.

Cong, L., et al., Multiplex Genome Engineering Using CRISPR/Cas Systems, Science, Feb. 15, 2013, vol. 339, pp. 819-823.

Sapranauskas, R., et al., The *Streptococcus thermophilus* CRISPR/Cas system provides immunity in *Escherichia coli*, Nucleic Acids Research, Aug. 3, 2011, vol. 39, No. 21, pp. 9275-9282.

Edgar, R. & Qimron, U., The *Escherichia coli* CRISPR System Protects from lambda Lysogenization, Lysogens, and Prophage Induction, Journal of Bacteriology, Oct. 1, 2010, vol. 192, No. 23, pp. 6291-6294.

Marraffini, L.A. & Sontheimer, E.J., CRISPR Interference Limits Horizontal Gene Transfer in Staphylococci by Targeting DNA, Science, Dec. 19, 2008, vol. 332, pp. 1843-1845.

Garneau, J.E., et al., The CRISPR/Cas bacterial immune system cleaves bacteriophage and plasmid DNA, Nature, Nov. 4, Nov. 4, 2010, vol. 468, pp. 67-71.

Bae, T., et al., Prophages of *Staphylococcus aureus* Newman and their contribution to virulence, Molecular Microbiology, 2006, pp. 1-13.

Third-Party Submission under 37 CFR 1.290 filed on Nov. 6, 2018 in U.S. Appl. No. 15/887,377, 5 pages.

Mei, J-M., et al., Identification of *Staphylococcus aureus* virulence genes in a murine model of bacteraemia using signature-tagged mutagenesis, Molecular Microbiology, 1997, vol. 26, No. 2, pp. 399-407.

Koonin, E.V., et al., Diversity, classification and evolution of CRISPR-Cas systems, Current Opinion in Microbiology, 2017, vol. 37, pp. 67-78.

Sorek, R., et al., CRISPR-Mediated Adaptive Immune Systems in Bacteria and Archaea, Annual Review of Biochemistry, Mar. 11, 2013, pp. 237-266.

Non-Final Rejection (Office Action) issued by United States Patent and Trademark Office on Jan. 27, 2020 for U.S. Appl. No. 14/766,675, 17 pages.

Fage, C., et al., Delivery of CRISPR-Cas systems using phage-based vectors, Current Opinion in Biotechnology, Dec. 23, 2020, vol. 68, pp. 174-180.

Makarova, K.S., et al., Evolution and classification of the CRISPR-Cas systems, Nature Reviews Microbiology, May 9, 2011, vol. 9, pp. 467-477.

United States Court of Appeals for the Federal Circuit, Judgment on Appeal from the United States Patent and Trademark Office, Patent Trial and Appeal Board in No. 106,132, Jul. 14, 2023, 1 page.

United States Court of Appeals for the Federal Circuit, Opinion on Appeal from the United States Patent and Trademark Office, Patent Trial and Appeal Board in No. 106,132, Jul. 14, 2023, 20 pages.

Non-Final Rejection (Office Action) issued by United States Patent and Trademark Office on Mar. 2, 2017 for U.S. Appl. No. 14/766,675, 9 pages.

Final Rejection (Office Action) issued by United States Patent and Trademark Office on Oct. 11, 2018 for U.S. Appl. No. 14/766,675, 12 pages.

Non-Final Rejection (Office Action) issued by United States Patent and Trademark Office on Apr. 18, 2019, for U.S. Appl. No. 14/766,675, 16 pages.

Hoyland-Kroghsbo, N.M., et al., A Quorum-Sensing-Induced Bacteriophage Defense Mechanism, mBio, Feb. 19, 2013, vol. 4, No. 1, e00362-12, pp. 1-8.

Del Pozo, J.L., et al., The Challenge of Treating Biofilm-associated Bacterial Infections, Translational Medicine, Aug. 2007, vol. 82, No. 2, pp. 204-209.

Non-Final Rejection (Office Action) issued by United States Patent and Trademark Office on Jan. 24, 2020 for U.S. Appl. No. 15/159,929, 17 pages.

Non-Final Rejection (Office Action) issued by United States Patent and Trademark Office on Sep. 18, 2017 for U.S. Appl. No. 15/159,929, 10 pages.

Final Rejection (Office Action) issued by United States Patent and Trademark Office on Apr. 27, 2018 for U.S. Appl. No. 15/159,929, 14 pages.

Declaration under 37 CFR 1.130(a) filed on Feb. 1, 2019 in U.S. Appl. No. 15/159,929, 2 pages.

Office Action Response and Request for Interference dated Feb. 18, 2020 in U.S. Appl. No. 15/159,929, 19 pages.

Redeclaration of Interference under 37 CFR 41.203(c) filed in United States Patent and Trademark Office in Interference No. 106,123 on Jul. 21, 2020, 6 pages.

Non-Final Rejection (Office Action) issued by United States Patent and Trademark Office on Apr. 2, 2019 for U.S. Appl. No. 15/159,929, 11 pages.

* cited by examiner

SEQUENCE SPECIFIC ANTIMICROBIALS

CROSS-REFERENCE TO RELATED APPLICATIONS

This application is a continuation of U.S. application Ser. No. 15/159,929, filed on May 20, 2016, which is a divisional of U.S. application Ser. No. 14/766,675, filed on Aug. 7, 2015, now U.S. Pat. No. 10,660,943, which is a National Phase of International Application No. PCT/US2014/015252, filed on Feb. 7, 2014, which claims priority to U.S. Provisional Application No. 61/761,971, filed on Feb. 7, 2013.

The present application is also a continuation of U.S. application Ser. No. 17/168,971, filed on Feb. 5, 2021, which is a divisional of U.S. application Ser. No. 16/877,010, filed on May 18, 2020, which is a continuation of U.S. application Ser. No. 14/766,675, filed on Aug. 7, 2015, now U.S. Pat. No. 10,660,943. U.S. application Ser. No. 17/168,971 is also a continuation of U.S. application Ser. No. 15/159,959, filed on May 20, 2016. U.S. application Ser. No. 17/168,971 is also a divisional of U.S. application Ser. No. 16/877,030, filed on May 18, 2020, now U.S. Pat. No. 11,135,273, which is a divisional of Ser. No. 15/159,959, filed on May 20, 2016.

The present application is also a continuation of U.S. application Ser. No. 17/088,297, filed on Nov. 3, 2020, which is a divisional of U.S. application Ser. No. 16/877,030, filed on May 18, 2020, now U.S. Pat. No. 11,135,273, which is a divisional of Ser. No. 15/159,959, filed on May 20, 2016.

The present application is also a continuation of U.S. application Ser. No. 17/088,302, filed on Nov. 3, 2020, which is a divisional of U.S. application Ser. No. 16/877,030, filed on May 18, 2020, now U.S. Pat. No. 11,135,273, which is a divisional of Ser. No. 15/159,959, filed on May 20, 2016.

The present application is also a divisional of U.S. application Ser. No. 16/877,010, filed on May 18, 2020, which is a continuation of U.S. application Ser. No. 14/766,675, filed on Aug. 7, 2015, now U.S. Pat. No. 10,660,943.

The disclosures of each of the afore-mentioned applications and patents are incorporated herein by reference.

SEQUENCE LISTING STATEMENT

The instant application contains a Sequence Listing which is submitted in .xml format and is hereby incorporated by reference in its entirety. Said .xml file is named "076091_00168_ ST26.xml", was created on Jan. 25, 2024, and is 46,115 bytes in size.

FIELD OF THE DISCLOSURE

The present disclosure is related to compositions and methods for selectively killing specific bacteria in mixed bacteria populations.

BACKGROUND OF THE DISCLOSURE

Advances in DNA sequencing technologies have revealed the diversity of complex microbial populations in many different environments. They have also provided evidence for the contributions that individual species make to the whole of the population and/or to their environment. Perhaps the most striking example of this is the human microbiome and its influence on human health. The study of the microbiome not only shows the importance of certain species for the human host, but has also revealed the undesired side-effects of traditional antimicrobials without killing specificity, which include promoting the emergence of antibiotic resistance and important negative effects on human health. These examples highlight the ongoing need for tools to accurately control and manipulate complex microbial consortia. The present disclosure meets these and other needs.

BRIEF SUMMARY OF THE DISCLOSURE

The present disclosure provides compositions and methods for selectively reducing the amount of antibiotic resistant and/or virulent bacteria in a mixed bacteria population, or for reducing any other type of unwanted bacteria in a mixed bacteria population. The compositions and methods involve targeting bacteria, wherein the targeted bacteria can be differentiated from other members of the population by at least one unique clustered regularly interspaced short palindromic repeats (CRISPR) targeted DNA sequence. Various embodiments of the compositions and methods of the disclosure are demonstrated using *Staphylococcus aureus* and CRISPR systems that employ nucleotide sequences directed to *S. aureus*, but the compositions and methods can be readily adapted, given the benefit of the present disclosure, to target any bacteria.

In one aspect the disclosure provides pharmaceutical compositions for selectively reducing the amount of bacteria in a mixed bacteria population wherein the composition comprises a pharmaceutically acceptable carrier and a packaged, recombinant phagemid. The phagemid comprises a CRISPR system, wherein the CRISPR system comprises nucleotide sequences encoding i) a CRISPR-associated (Cas) enzyme; and ii) a targeting RNA selected from at a) least one bacterial chromosome targeting RNA; or b) at least one plasmid targeting RNA; or a combination of a) and b). In embodiments, the Cas enzyme encoded by the CRISPR system is a wild type Cas enzyme, or a modified Cas enzyme. In embodiments, the targeting RNA is selected from a CRISPR RNA (crRNA) and a guide RNA. If the targeting RNA is a crRNA, the phagemid further comprises a sequence encoding a separately transcribed trans-activating CRISPR crRNA (tracrRNA) sequence. In embodiments, the targeting RNA is directed to a bacterial virulence gene or an antibiotic resistance gene in the bacteria. Such gene targets can be on the bacterial chromosome, a plasmid in the bacteria, or both. In embodiments, the targeting RNA is specific for a DNA sequence present in a virulent and/or antibiotic resistant bacteria, but the DNA sequence is not present in non-virulent and non-antibiotic resistant bacteria in the bacterial population.

In another aspect the disclosure provides methods for reducing the amount of virulent and/or antibiotic resistant bacteria or plasmids in a bacterial population. The method comprises contacting the bacterial population with a pharmaceutical composition as described herein, wherein contacting the bacterial population is such that at least some of the phagemids are introduced into at least some of the bacteria in the bacterial population and, subsequent to the introduction of the phagemids, at least the targeting RNA and the Cas enzyme are produced. Subsequent to production of at least the targeting RNA and the Cas enzyme, the amount of unwanted bacteria in the population, such as the amount of virulent and/or antibiotic resistant bacteria, or plasmids in the mixed bacterial population, is reduced.

In another aspect, the disclosure includes a method for personalized therapy for an individual in need of therapy for a bacterial infection. The method comprises obtaining a biological sample from the individual and determining a plurality of bacterial DNA sequences from the sample. The biological sample can be any biological sample, including but not necessarily limited to a liquid biological sample, such as blood, mucous, serum, cerebrospinal fluid, saliva, and urine, or a solid biological sample, such as a biopsy of any tissue, or it can comprise a sample obtained by using an implement such as a swab. The biological sample can be tested directly or it can be processed before determining the sequences. Based on determining the sequences one or more virulent and/or antibiotic resistant bacterial species are identified, thus providing one or more DNA sequences that are unique to those bacteria. Based on the unique DNA sequences a phagemid CRISPR system is developed that comprises targeting RNA that target the unique sequence(s) present in the virulent and/or antibiotic resistant bacterial species. The phagemids are encapsidated (i.e., packaged) in phage proteins and the packaged phagemids are mixed with a pharmaceutically acceptable carrier to provide a pharmaceutical composition. The pharmaceutical composition is administered to the individual from which the biological sample was obtained. The administration is such that at least some of the phagemids are introduced into at least some of the virulent and/or antibiotic resistant bacteria in or on the individual and, subsequent to the introduction of the phagemids, at least the targeting RNA and the Cas9 enzyme are produced, and wherein the amount of virulent and/or antibiotic resistant bacteria and/or the amount of targeted plasmids in the bacteria is reduced. Thus the method facilitates reducing the amount of pathogenic bacteria on or in the individual, but the amount of non-pathogenic bacteria is not reduced.

DETAILED DESCRIPTION OF THE DISCLOSURE

Figure 1:
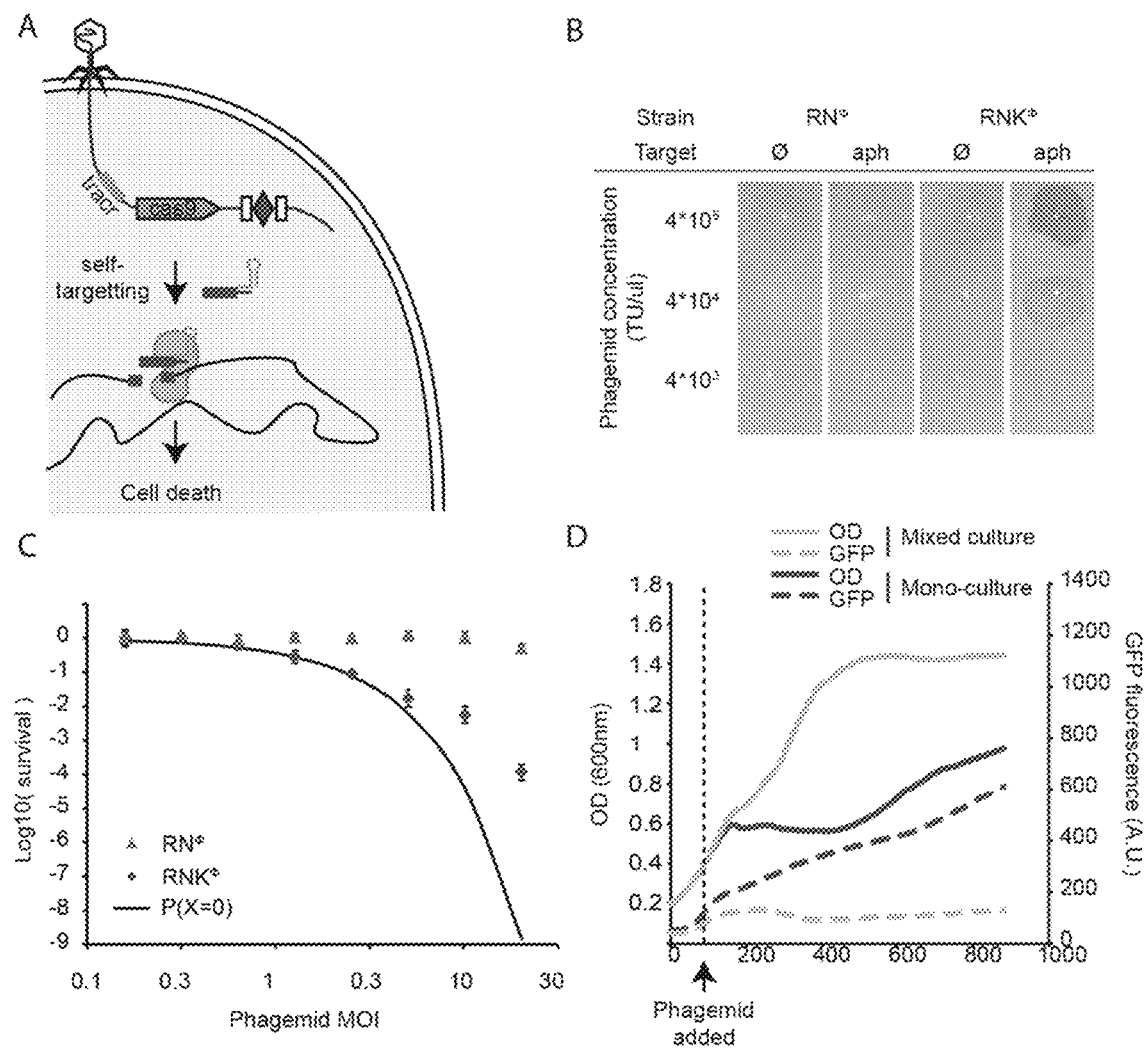
FIG. 1 shows a sequence-specific killing of *S. aureus* by a phagemid-delivered CRISPR system. (A) The ΦNM1 phage delivers the pDB121 phagemid to *S. aureus* cells. pDB121 carries the *S. pyogenes* tracrRNA, cas9 and a programmable CRISPR array sequences. Expression of cas9 and a self-targeting crRNA leads to chromosome cleavage and cell death. (B) Lysates of pDB121 phagemid targeting the aph-3 kanamycin resistance gene or a non-targeting control were spotted on top-agar lawns of either RN<sup>Φ</sup> or RNK<sup>Φ</sup> cells. (C) Treatment of RN<sup>Φ</sup> (blue triangles) or RNK<sup>Φ</sup> (red diamonds) with pDB121::aph at various MOI. Survival is computed as the ratio of CFU recovered after treatment over CFU from an untreated sample of the same culture (mean±s.d.). The black curve represents the probability that a cell does not receive any phagemid making the assumption that all cells have the same chance to receive a phagemid. (D) Time course of the treatment by pDB121::aph of RNK<sup>Φ</sup>/pCN57 (GFP reporter plasmid) cells either in a monoculture or in a mixed culture with non-targeted RN<sup>Φ</sup> cells.

Traditional antimicrobials target conserved cellular pathways and therefore cannot selectively kill specific members of a complex microbial population. However, there are many instances when the survival of specific members of the population is desirable, for example for the manipulation of the human microbiome. Therefore the ability to remove specific members of a microbial consortium would be desirable, and is achieved by the present disclosure. In particular, we demonstrate several representative, programmable, sequence-specific antimicrobials using the RNA-guided Cas9 nuclease and a phagemid system for its delivery into *Staphylococcus aureus*.

As is recognized in the art, a CRISPR site is a distinctive DNA locus (i.e., an array or cluster of DNA sequences) found in the genomes of many bacteria and archaea. It has been reported that CRISPR sequences can function as a type of "immune system" that help bacteria defend against phage infections (see, for example, Barrangou et al., "CRISPR Provides Acquired Resistance Against Viruses in Prokaryotes," Science 315:1709-12 (March 2007); Deveau et al., J. Bacteriol. 190(4): 1390-1400 (February 2008); Horvath et al., J. Bacteriol. 190(4): 1401-12 (February 2008)).

The present disclosure in part exploits the evolutionary battle between phage and bacteria by co-opting the phage to selectively kill specific bacteria in a sequence specific manner that is controlled by deliberate programming of the novel phagemid-CRISPR systems described herein. In this regard, we show that after programming Cas9 to target virulence genes, phagemid treatment specifically kills virulent, but not avirulent, staphylococci. Phagemids can also specifically destroy staphylococcal plasmids that spread antibiotic resistance genes and immunize avirulent cells against the uptake of such plasmids. Sequence-specific killing was also achieved using a murine skin colonization model, demonstrating the broad applicability of Cas9-based, programmable antimicrobials. Additionally, we demonstrate sequence specific repression of bacterial transcription using a modified Cas9 CRISPR system. Thus, the present disclosure provides a widely applicable and adaptable system for selectively killing only certain bacteria in a population of bacteria, as well as for eliminating specific genetic elements, such as plasmids, from a population of bacteria, and maintain eradication and/or low levels of such plasmids. Accordingly, given the benefit of the present disclosure, the compositions and methods described herein can be readily adapted to selectively kill any bacteria and/or reduce or eliminate any bacterial extra-chromosomal genetic elements in a mixed population of bacteria to provide a therapeutic and/or prophylactic benefit, or for any other setting or purpose where a reduction in specific bacterial populations and/or genetic elements would be desirable. These include but are not necessarily limited to using the compositions on medical devices or other medical implements to reduce or eliminate harmful bacteria, or in non-medical applications where it is desirable to inhibit or eliminate specific bacterial growth on non-medical objects or surfaces. Therefore, in general, and as will be described more fully below, embodiments of the present disclosure provide pharmaceutical compositions for selectively reducing the amount of antibiotic resistant and/or virulent bacteria in a bacteria population, or for reducing any other type of bacteria in a bacteria population, wherein the targeted bacteria can be differentiated from other members of the population by way of at least one unique CRISPR DNA sequence. As used herein, bacteria that are virulent and/or antibiotic resistant can be considered to be "pathogenic" bacteria.

In embodiments, the composition comprises a packaged, recombinant phagemid, wherein the phagemid comprises a CRISPR system, wherein the CRISPR system comprises nucleotide sequences encoding a Cas enzyme and a targeting RNA selected from at least one chromosome targeting RNA, or at least one plasmid targeting RNA, or a combination thereof. As described further below, in embodiments, the CRISPR system can be configured to target only a specific type of bacteria by targeting a specific sequence in the bacteria, such as a DNA sequence present in a virulent and/or antibiotic resistant bacteria, wherein that DNA sequence is not present in non-virulent and non-antibiotic resistant bacteria that are in the same bacteria population as the targeted bacteria.

Unless defined otherwise herein, all technical and scientific terms used herein have the same meaning as commonly understood by one of ordinary skill in the art to which this disclosure pertains.

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The term "bacteria" as used herein refers to any of the prokaryotic microorganisms that exist as a single cell or in a cluster or aggregate of single cells.

The term "pharmaceutically acceptable carrier" as used herein refers to a substantially non-toxic carrier for administration of pharmaceuticals in which the compound will remain stable and bioavailable. Adding a pharmaceutically acceptable carrier to other components of the compositions described herein is considered to yield "pharmaceutical compositions." The pharmaceutically acceptable carrier contained in the pharmaceutical composition can be any carrier which is used in pharmaceutical formulations, examples of which include but are not limited to, lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition may further include a lubricant, a humectant, an emulsifier, a suspending agent, and a preservative. Details of suitable pharmaceutically acceptable carriers and formulations can be found in Remington's Pharmaceutical Sciences (19th ed., 1995), which is incorporated herein by reference. The pharmaceutical composition can further comprise an additional active ingredient(s), such as an antibiotic.

The pharmaceutical compositions can be provided in the form of pills, tablets, coated tablets, lozenges, capsules, solutions, syrups, emulsions, suspensions, as aerosol mixtures, gels, foams, sols, slurries, ointments, creams or tinctures, and can also include other components, such as liposomes, microsomes, nanoparticles, and any other suitable vehicle for delivering a packaged phagemid of the disclosure to a subject or to any object or non-living surface wherein inhibition or elimination of specific bacteria is desired.

For administering to a subject in need thereof, the pharmaceutical composition can be administered orally, parenterally, topically, nasally, vaginally, or rectally. Parenterally administration includes intravenous, intra-abdominal, intramuscular, intraperitoneal or transdermal administration. A suitable dosage amount of the pharmaceutical composition of the present disclosure can vary depending on pharmaceutical formulation methods, administration methods, the patient's age, body weight, sex, type and location of bacterial infection, diet, administration time, administration route, an excretion rate. In embodiments, a pharmaceutical composition can be administered with a dosage of $10^1$-$10^{14}$ PFU/kg (body weight). Such a concentration can be use, for example, as a single or daily dose for a period of time such that the unwanted bacteria are reduced to a satisfactory level or are eliminated.

The term "treating" as used herein includes abrogating, substantially inhibiting, slowing or reversing the progression of a condition, substantially ameliorating clinical or aesthetical symptoms of a condition, substantially preventing the appearance of clinical or aesthetical symptoms of a condition, or protecting from harmful or annoying stimuli.

The terms "inhibiting" "inhibit" and "inhibition" as used herein are used to refer to reducing the amount or rate of a process, to stopping the process entirely, or to decreasing, limiting, or blocking the action or function thereof. Inhibition can include a reduction or decrease of the amount, rate, action function, or process by at least 5%, up to and include at least 99% when compared to a suitable reference.

The term "variant" and its various grammatical forms as used herein refers to a nucleotide sequence or an amino acid sequence with substantial identity to a reference nucleotide sequence or reference amino acid sequence, respectively. The differences in the sequences may be the result of changes, either naturally or by design, in sequence or structure. Natural changes may arise during the course of normal replication or duplication in nature of a particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence. For example, in embodiments, the Cas used in the present disclosure is a wild type or mutant Cas expressed recombinantly. The Cas sequence can comprise the wild type amino acid sequence expressed by any bacteria that encodes a Cas. In one embodiment, the Cas is a Cas9 having a Cas9 amino acid sequence encoded by *Streptococcus pyogenes*. In one embodiment, the Cas9 is a variant Cas9 that comprises one or more mutations. In an embodiment, the Cas9 comprises one or more mutations that lessen or eliminate its nuclease activity, but its DNA binding ability is retained. In one embodiment, the mutations comprise a D10A and/or an H840A change in the *Streptococcus pyogenes* Cas9 amino acid sequence. The reference sequence of *S. pyogenes* is available under GenBank accession no. NC_002737, with the cas9 gene at position 854757-858863. The *S. pyogenes* Cas9 amino acid sequence is available under number is NP_269215. These sequences are incorporated herein by reference as they were provided on the priority date of this application or patent.

In an embodiment, a Cas9 comprising the double mutant D10A and an H840A is used for sequence specific transcription repression in bacteria is connection with a CRISPR system as further described herein. Thus, the present disclosure provides in various embodiments modified CRISPR systems.

The present disclosure provides modified CRISPR systems that differ from those which naturally occur in bacteria. Previous attempts to provide modified CRISPR systems have been described, such as in WO2013176772. However, in contrast to the present case, these disclosures do not include any description of compositions and methods for selectively reducing pathogenic, i.e., virulent, and/or antibiotic resistant members of a bacterial population, and do not include a description of phagemids or using phagemids to achieve this result.

With respect to CRISPR systems, as will be recognized by those skilled in the art, the structure of a naturally occurring CRISPR locus includes a number of short repeating sequences generally referred to as "repeats." The repeats occur in clusters and up to 249 repeats have been identified in a single CRISPR locus and are usually regularly spaced by unique intervening sequences referred to as "spacers." Typically, CRISPR repeats vary from about 24 to 47 bp in length and are partially palindromic. The repeats are generally arranged in clusters (up to about 20 or more per genome) of repeated units. The spacers are located between two repeats and typically each spacer has a unique sequences that are from about 20-72 bp in length. Many spacers are identical to or have high homology with known phage sequences. In addition to repeats and spacers, a CRISPR locus also includes a leader sequence and often a set of two to six associated Cas genes. The leader sequence typically is an AT-rich sequence of up to 550 bp directly adjoining the 5' end of the first repeat. New repeat-spacer units are believed to be almost always added to the CRISPR locus between the leader and the first repeat.

Generally, it is thought that the proteins encoded by the associated Cas genes act as a bacterial "immune system" that confer resistance against phages (also referred to as 'CRISPR interference'). At the molecular level, CRISPR interference can be divided into three phases. In the adaptation phase, new repeat-spacer units are incorporated to re-program CRISPR interference against new invasive nucleic acids, allowing the cell to adapt rapidly to the invaders present in the environment. As described more fully below, during the crRNA biogenesis phase, repeat/spacer arrays are transcribed as a long precursor that is cleaved within repeat sequences and processed into small CRISPR RNAs (crRNAs) by Cas endoribonucleases. crRNAs retain spacer sequences that specify the targets of CRISPR interference. In the targeting phase crRNAs are used as antisense guides in Cas/crRNA ribonucleoprotein complexes that cleave the nucleic acids of mobile genetic elements carrying a cognate sequence, known as the protospacer, also referred to herein as "spacers." In addition to spacer-target complementarity, the presence of a conserved short tri- or tetra-nucleotide sequence, known as the protospacer adjacent motif (PAM), is involved in CRISPR interference.

As described above, the present disclosure differs in multiple respects from CRISPR systems that exist naturally. In particular, the present disclosure provides modified CRISPR systems that are encoded by phagemids. Phagemids are plasmids modified to carry a phage packaging site and may also encode phage proteins. Phagemids may comprise, in general at least a phage packaging site and an origin of replication (ori). In embodiments, phagemids of the present disclosure encode phage packaging sites and/or proteins involved in phage packaging. In embodiments, the phagemids include a packaging site and are packaged by a phage that is intended to be introduced into a population of bacteria according to the methods of this disclosure. In embodiments, the phage is of a type that selectively infects a pathogenic type of bacteria, or a type of bacteria that can have pathogenic and non-pathogenic members in a mixed bacteria population, or can infect different types of bacteria in a mixed bacteria population. In embodiments, the phage is specific for a particular bacterial genus, species or strain. In an embodiment, the phage is specific for a bacterial strain that is a member of one of: Streptococcus, Staphylococcus, Clostridium, Bacillus, Salmonella, Helicobacter pylori, Neisseria gonorrhoeae, Neisseria meningitidis, or Escherichia coli. In embodiments, the phage is specific for Staphylococcus aureus. In embodiments, the phage is a staphylococcal ΦNM1 phage.

In embodiments, the phagemids encode one or more bacteriophage proteins. In one embodiment, the phagemids comprise a combination of the rinA, terS and terL genes. The phagemids provided by the instant disclosure undergo replication, expression of encoded proteins, and packaging. The packaging occurs at least in part because of the packaging signals they encode and by expression of the packaging proteins, either by the phagemids alone, or in conjunction with a suitable helper phage. When encapsidated by phage protein the phagemids are considered to be "packaged phagemids" or a "packaged phagemid." Thus, in embodiments, the present disclosure includes isolated phagemids, as well as isolated packaged phagemids, and packaged phagemids which are provided as a component of compositions, including but not necessarily limited to pharmaceutical composition(s). The present disclosure includes all methods of making phagemids and packaged phagemids that are described herein.

The recombinant phagemids encode in various embodiments a CRISPR system that is engineered to selectively kill only a subset of bacteria or reduce only a specific plasmid within a bacterial population, or to do both. The system includes a sequence encoding a CRISPR-associated (Cas) enzyme, such as the S. pyogenes Cas9 and/or a modified version of it described above, and a targeting RNA. A "targeting RNA" is an RNA that, when transcribed from the portion of the CRISPR system encoding it, comprises at least a segment of RNA sequence that is identical to (with the exception of replacing T for U in the case of RNA) or complementary to (and thus "targets") a DNA sequence in the bacterial chromosome, or a sequence on a plasmid within the targeted bacteria. The CRISPR systems of the present disclosure can encode more than one targeting RNA, and the targeting RNAs can be directed to one or more sequences in the bacterial chromosome, or plasmid, or combinations thereof. The sequence of the targeting RNA thus dictates what is targeted by the CRISPR system carried by the phagemids. Accordingly, any distinct CRISPR sequence that is specific for any particular type of bacteria that would be desirable to kill can be readily designed based on the present disclosure and the knowledge of those skilled in the art. For example, in any bacterial population which comprises or would be suspected to comprise bacteria that would be desirable to kill, a CRISPR sequence encoding a targeting RNA directed to any CRISPR site unique to those bacteria can be designed. Accordingly, a targeting RNA sequence determines the DNA sequence in a bacteria that will be subject to nuclease cleavage by the Cas that is part of the CRISPR system(s) described herein.

In embodiments, the disclosure includes CRISPR systems on phagemids which target virulent bacteria within a bacteria population. The bacterial population can comprise one type of bacteria, but with virulent and non-virulent members, or the bacterial population can comprise a plurality of bacterial species, with only certain species having virulent and non-virulent members in the population. In embodiments, a mixed bacteria population comprises at least two different strains or species of bacteria. In embodiments, the mixed bacteria population comprises from between two distinct types of bacteria, to up to a thousand distinct types of bacteria, or more. In embodiments, the bacteria population comprises a plurality of bacteria types that have been identified as part of the human microbiome, such as those bacteria that have been identified by the Human Microbiome Project (HMP) Consortium which employed DNA-sequencing to identify and catalogue the thousands of microorganisms, including bacteria, that make up the human microbiota. In embodiments, the population of bacteria are only present in a specific site of an individual, such as the skin, or a particular location on the skin, or a particular mucosal tissue.

The term "virulent" as used herein means a bacteria that can cause a bacterial disease or infection. In embodiments, virulent bacteria are those that cause a bacterial disease or infection in a human subject who does not have a compromised immune system.

Typically, virulent bacteria will produce certain proteins which are referred to as "virulence factors." Virulent bacteria are distinguishable from those bacteria that normally colonize one or more of a healthy host's tissue and for which they are thus undesirable to kill under ordinary therapeutic circumstances because the latter generally do not express virulence factors, or express lower amounts of virulence factors relative to virulent bacteria. As discussed above, the present disclosure includes in embodiments CRISPR systems which comprise sequences encoding targeting RNA directed to bacterial DNA sequences which encode virulence factors. Such virulence factors include but are not necessarily limited to bacteria proteins that are involved in pathogenic adhesion, colonization, invasion, or immune response inhibitors, or toxins. In embodiments, the virulence factors are selected from proteases, lipases, endonucleases, hemolysins, endotoxins and exotoxins. The sequences of bacterial genes from a wide array of bacteria types that encode these and other virulence factors are known in the art. Virulence factors can be encoded on the bacterial chromosome, or on a plasmid in the bacteria, or both. In embodiments, the virulence factor is encoded by a bacterial superantigen gene, such as a superantigen enterotoxin gene, one non-limiting example of which is the S. aureus Sek gene. Additional virulence factors for S. areus include but are not limited to cytolitic toxins, such as α-hemolysin, β-hemolysin, γ-hemolysin, leukocidin, Panton-Valentine leukocidin (PVL); exotoxins, such as toxic shock syndrome toxin-1 (TSST-1); enterotoxins, such as SEA, SEB, SECn, SED, SEE, SEG, SEH, and SEI, and exfoliative toxins, such as ETA, ETB.

Homologues of all of these toxins expressed by other types of bacteria are contemplated as virulence gene targets as well.

In embodiments, a virulent type of bacteria, or in certain cases a non-virulent type bacteria, may also comprise an antibiotic resistant gene. Antibiotic resistance genes carried by a variety of bacteria are known in the art and the sequences of antibiotic resistance genes in any particular bacteria can be determined if desired. In certain non-limiting embodiments the present disclosure includes CRISPR systems which comprise sequences encoding targeting RNA that is directed to bacterial DNA sequences which comprise antibiotic resistance genes. In embodiments, the resistance gene confers resistance to a narrow-spectrum beta-lactam antibiotic of the penicillin class of antibiotics. In embodiments, the resistance gene confers resistance to methicillin (e.g., methicillin or oxacillin), or flucloxacillin, or dicloxacillin, or some or all of these antibiotics. Thus, in one embodiment, the CRISPR system is suitable for selectively killing what has colloquially become known as methicillin-resistant S. aureus (MRSA) which in practice refers to strains of S. aureus that are insensitive or have reduced sensitivity to most or all penicillins. In another embodiment, the CRISPR system is suitable for killing vancomycin resistant S. aureus (VRSA). In embodiments, vancomycin resistant S. aureus may also be resistant to at least one of linezolid (ZYVOX™), daptomycin (CUBICIN™), and quinupristin/dalfopristin (SYNERCID™).

If in an antibiotic resistance gene is present on a plasmid, and the CRISPR system provided only targets the plasmid (which does not necessarily mean the antibiotic resistance gene itself is targeted, so long as the plasmid on which it resides is targeted), this disclosure thereby includes converting a population of bacteria from antibiotic resistant to an antibiotic sensitive population. If desired an appropriate antibiotic can then be used to rid a subject of all or most of the bacteria that have accordingly been sensitized to the antibiotic. Additional antibiotic resistant genes include but are not limited to fosfomycin resistance gene fosB, tetracycline resistance gene tetM, kanamycin nucleotidyltransferase aadD, bifunctional aminoglycoside modifying enzyme genes aacA-aphD, chloramphenicol acetyltransferase cat, mupirocin-resistance gene ileS2, vancomycin resistance genes vanX, vanR, vanH, vraE, vraD, methicillin resistance factor femA, fmtA, mecI; streptomycin adenylyltransferase spc1, spc2, ant1, ant2, pectinomycin adenyltransferase spd, ant9, aadA2.

The targeting RNA encoded by the CRISPR system can be a CRISPR RNA (crRNA) or a guide RNA. The sequence of the targeting RNA is not particularly limited, other than by the requirement for it to be directed to (i.e., having a segment that is the same as or complementarity to) a CRISPR site that is specific for the type of bacteria and/or plasmid that is to be killed or eliminated from the bacteria, respectively. In this regard, as described briefly above, a target sequence in the bacteria comprises a specific sequence on its 3' end referred to as a protospacer adjacent motif or "PAM". The PAM is in the targeted DNA, but a targeting RNA directed to a sequence adjacent to the PAM may or may not have the PAM as a component. In general, the present disclosure is pertinent to target spacer sequences that are subject to cleavage by any Type II CRISPR system, and thus the target sequences conform to the well-known N12-20NGG motif, wherein the NGG is the PAM sequence. It will be recognized that 20 nts is the size of the homology sequence in processed crRNA, but, for example, when using a guide RNA that is not processed, the homology sequence can be more than 20 nts, such as up to 40 or more nts. Thus, in embodiments, a targeting RNA used in this disclosure will comprise or consist of a segment that is from 12-40 nucleotides in length. If the phagemid encodes a crRNA, including but not necessarily limited to a pre-crRNA, the phagemid will also encode a tracrRNA. In various embodiments, the tracrRNA can comprise a segment that is complementary to a pre-crRNA, such that a portion of the tracrRNA and pre-crRNA can form an RNA duplex. The RNA duplex is cleaved by RNase III, resulting in the formation of a crRNA/tracrRNA hybrid complex. This hybrid functions as a guide for Cas, which cleaves the target sequence in the bacteria. In general, a tracrRNA used in embodiments of the present disclosure will comprise or consist of from 40 to 200 nucleotides, inclusive, and including all integers and ranges there between. tracrRNA produced in S. pyogenes is a 171 nt RNA which is then processed into 89 or 75 nt fragments. There are a wide variety of publicly available resources that can be used to design suitable tracrRNA sequences and such tracrRNA sequences can be adapted for use with embodiments of the present disclosure. To provide one illustrative embodiment, the S. pyogenes 171 species of the tracrRNA is:

(SEQ ID NO: 30)
AGTATTAAGTATTGTTTTATGGCTGATAAATTTCTTTGAATTTCTCCTTG

ATTATTTGTTATAAAAGTTATAAAATAATCTTGTTGGAACCATTCAAAAC

AGCATAGCAAGTTAAAATAAGGCTAGTCCGTTATCAACTTGAAAAAGTGG

CACCGAGTCGGTGCTTTTTTT.

The 89 nt species is:
(SEQ ID NO: 31)
GTTGGAACCATTCAAAACAGCATAGCAAGTTAAAATAAGGCTAGTCCGTT

ATCAACTTGAAAAAGTGGCACCGAGTCGGTGCTTTTTTT.

The 75 nt species is:
(SEQ ID NO: 32)
AAACAGCATAGCAAGTTAAAATAAGGCTAGTCCGTTATCAACTTGAAAAA

GTGGCACCGAGTCGGTGCTTTTTTT.

In an embodiment, the sequence of the mature crRNA comprises 20 nt of sequence that is homologous to the target, followed by: -GTTTTAGAGCTATGCTGTTTTG (SEQ ID NO: 33). To illustrate one non-limiting embodiment, a segment of a CRISPR array comprising two spacers can have the sequence:
GTTTTAGAGCTATGCTGTTTTGAATGGTCC-CAAAAC-(spacer 1 sequence (30 nt))-GTTTTAGAGC-TATGCTGTTTTGAATGGTCCCAAAAC-(spacer 2 sequence (30 nt))-GTTTTAGAGCTATGCTGTTTT-GAATGGTCCCAAAAC. The GTTTTAGAGC-TATGCTGTTTTGAATGGTCCCAAAAC corresponds to SEQ ID NO:34. To provide one non-limiting example of a repeat-spacer sequence, combining the repeat sequence shown in SEQ ID NO:34 with the aph spacer site as shown in Table 1 as SEQ ID NO:1 yields:
5'-TCATGAGTGAGGCCGATGGCGTCCTTTGCT-GTTTTAGAGCTATGCTGTTTTG 3'(SEQ ID NO:39). RNA forms of these sequences have the T replaced with U.

In general a mature crRNA, meaning a crRNA that is complexed with a Cas during cleavage of a DNA target sequence, will comprise or consist of from 20-60 nucleotides. In embodiments, a crRNA comprises or consists of 20, 21, 22, 23, 24, 25, 26, 27, 28, 29, 30, 31, 32, 33, 34, 35, 36, 37, 38, 39 or 40 nt nt of the spacer (targeting) sequence followed by 19-36 nt of repeat sequence. In specific and non-limiting embodiments, the targeting RNA will comprise or consist of a segment that targets any one of the genes for which representative spacer sequences are presented in Table 1. It will be recognized that where T is presented in the sequences of Table 1 it will be replaced by U in the targeting RNA. The targeting RNA can therefore comprise a segment that itself comprises or consists of a sequence that is identical to any of the sequences presented in Table 1 wherein each T is replace by U.

In embodiments, instead of separately providing for transcription of a tracrRNA and a crRNA, the disclosure includes providing a phagemid which encodes a guide RNA that contains both a tracrRNA segment and a crRNA segment. This configuration abrogates the requirement for separate transcription initiation sites, separate promoters, and the like, and as a consequence produces a crRNA-tracrRNA fused hybrid RNA. In general, a guide RNA sequence will comprise or consist of between 40-200 nucleotides of tracrRNA sequence. In embodiments, from 40-100 nucleotides of tracrRNA is present in a guide RNA. In one embodiment, 85 nucleotides of tracrRNA are present in a guide RNA. With respect to the spacer (targeting) segment of a guide RNA or the targeting portion of a crRNA can comprise or consist of 20, 21, 22, 23, 24, 25, 26, 27, 28, 29, 30, 31, 32, 33, 34, 35, 36, 37, 38, 39 or 40 nt of the spacer (targeting) sequence, and may further comprise 19-36 nt of repeat sequence.

In addition to the compositions described above, the present disclosure also provides methods for selectively reducing the amount of virulent and/or antibiotic resistant bacteria in a bacterial population. The method comprises contacting the bacterial population with a composition comprising a packaged phagemid, wherein the phagemid encodes a CRISPR system as described herein, wherein the contacting the bacterial population is such that at least some of the phagemids are introduced into at least some of the bacteria in the bacterial population and, subsequent to the introduction of the phagemids, at least the targeting RNA and the Cas enzyme are produced, and wherein the amount of the virulent and/or antibiotic resistant bacteria in the mixed bacterial population is reduced, while non-virulent and/or non-antibiotic resistant bacteria in the population are not reduced from the effects of the CRISPR system. In embodiments, the compositions and methods are directed to selectively reducing virulent and/or antibiotic resistant *S. aureus* in a mixed population of bacteria. In embodiments, at least 50%-99.9% of the targeted bacteria, inclusive, and including all integers to the first decimal place there between and all ranges there between, are killed by practicing an embodiment of this disclosure.

It will be apparent that this disclosure provides broadly applicable compositions and methods for prophylaxis and/or therapy of diseases and/or bacterial infections that are caused by or are suspected of being caused by known strains of virulent and/or antibiotic resistant bacteria having known gene sequences that are suitable for targeting with pre-made CRISPR encoding, packaged phagemid containing compositions.

In another aspect the disclosure includes a method for personalized prophylaxis and/or therapy of bacterial infections or diseases. The method comprises obtaining a sample of a bacterial population from an individual in need of prophylaxis and/or therapy for a condition associated with a bacterial infection, and determining DNA sequences for a plurality of bacterial species in the sample population. By analyzing the DNA sequences, the presence and/or amount of virulent or otherwise undesirable bacteria can be determined and a CRISPR system as described herein can be designed using targeting RNA directed to unique CRISPR site DNA sequences in the bacteria associated with the condition. The DNA sequences of the bacteria in the sample can be analyzed using any suitable technique. As noted above, DNA sequencing has been used to identify and catalog many bacteria that make up the human microbiota. Further, many sequencing approaches, such as so-called deep sequencing, massively parallel sequencing and next generation sequencing can be used and such services are offered commercially by a number of vendors. A composition comprising a CRISPR system designed to target only pathogenic bacteria in the sample is administered to the individual such that at least some of the phagemids are introduced into at least some of the unwanted bacteria in or on the individual and, subsequent to the introduction of the phagemids, at least the targeting RNA and the Cas9 enzyme are produced, subsequent to which the amount of unwanted bacteria (and/or the amount of unwanted plasmids) in or on the individual is reduced. Other, beneficial bacteria are accordingly not affected by the CRISPR system, even if a phagemid is introduced into them.

It will be apparent from the foregoing that various embodiments of the disclosure provide compositions and methods suitable for treating a subject for any condition that is caused by or is positively correlated with the presence of unwanted bacteria. In embodiments, the method is suitable for prophylaxis and/or therapy for a subject for any one or combination of conditions associated with an infection by any one or combination of *Streptococcus, Staphylococcus, Clostridium, Bacillus, Salmonella, Helicobacter pylori, Neisseria gonorrhoeae, Neisseria meningitidis,* or *Escherichia coli*. In embodiments, the individual is in need of treatment for or is at risk of contracting a nosocomial infection. In embodiments, the individual is an immunocompromised individual. In embodiments, the individual is in need of treatment for or is at risk for contracting a bacterial infection of the skin and/or a mucosal surface. In embodiments, the individual is in need of treatment for an infection of *S. aureus*. In embodiments, the subject is a human patient. In embodiments, the compositions and methods are adapted for veterinary medicine purposes for treating non-human animals, including but not necessarily limited to canines, felines, equines, and bovines.

In one embodiment, the method for personalized prophylaxis and/or therapy comprises obtaining a sample from one or more individuals, and/or one or more surfaces, wherein the individuals and/or the surfaces have been exposed to or are suspected of having been exposed to a pathogenic bacteria, identifying CRISPR target sites in the pathogenic bacteria, and administering to the individual a composition comprising packaged phagemids which comprise a CRISPR system designed to kill the pathogenic bacteria. In embodiments, the individuals and/or the surfaces were purposefully exposed to the pathogenic bacteria.

The following examples are presented to illustrate the present disclosure. They are not intended to be limiting in any manner. In some aspects, these Examples include routine techniques and methods used in the field of genetic engineering and molecular biology that are not otherwise described. The following resources include descriptions of general methodology useful in accordance with the disclosure: Sambrook et al., Molecular Cloning: A Laboratory Manual (4th Ed., 2012); Kreigler, Gene Transfer and Expression: A Laboratory Manual (1993) and Ausubel et al., Eds. Current Protocols in Molecular Biology (1995). These general references provide definitions and methods known to those in the art. However, it is not intended that the present disclosures be limited to any particular methods, protocols, and reagents described, as these may vary in ways that will be understood by the skilled artisan.

Example 1

Figure 4:
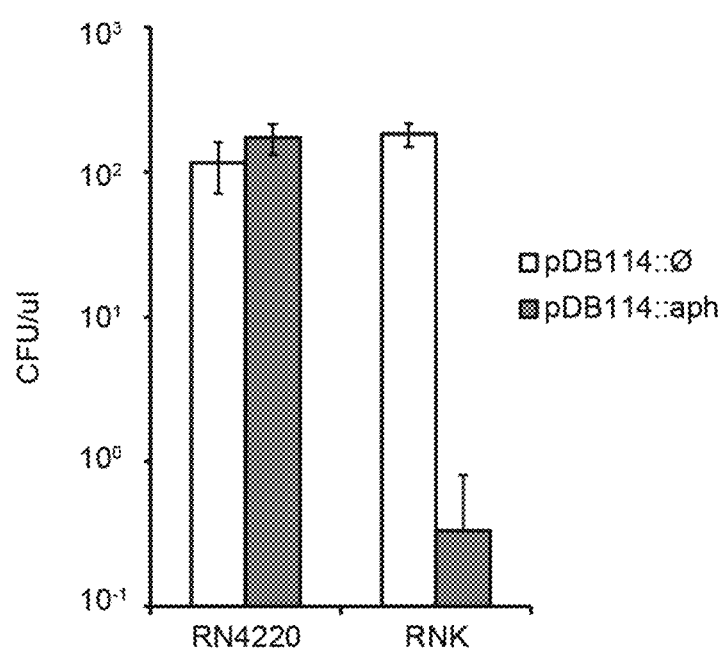
FIG. 4 shows an example of how the *S. pyogenes* CRISPR-Cas system can be programmed to kill *S. aureus*. Plasmid pDB114 carries the *S. pyogenes* tracrRNA, cas9 and a minimal array containing two repeats separated by a sequence containing BsaI restriction sites used to clone crRNA guide sequences using annealed oligonucleotides. pDB114 was programmed to target the aph-3 kanamycin resistance gene and transformed either in electrocompetent RN4220 cells or RNK cells carrying aph-3 in the chromosome. Chloramphenicol resistant CFU obtained in three independent assays are reported (mean±s.d.).

In the present disclosure we demonstrate the feasibility of using packaged phagemids encoding CRISPR systems as sequence-specific antimicrobials that facilitate the selective killing bacteria within a heterogeneous bacteria population. To demonstrate specific embodiments of this approach, we used the cas9 gene and its RNA guide/s sequences using a phagemid, a plasmid designed to be packaged in phage capsids (FIG. 1A). We demonstrate the general applicability of this approach by using *Staphylococcus aureus*. We show that we can selectively kill antibiotic-resistant and/or virulent *Staphylococcus aureus* strains which for a variety of well-known reasons are pertinent to public health. In particular, staphylococci are at the same time the predominant members of the human skin microbiota and one of the most common causes of nosocomial infections. The recent increase in staphylococcal pathogenicity is largely the result of the transfer of antibiotic resistance and virulence genes via conjugative plasmids and other mobile genetic elements that has led to the rise of hospital- and community-acquired methicillin- and vancomycin-resistant *Staphylococcus aureus* (MRSA and VRSA, respectively) strains that are very difficult to treat. To corroborate that Cas9 cleavage of chromosomal sequences is sufficient to kill staphylococci, we inserted *Streptococcus pyogenes* cas9, tracrRNA (trans-activating crRNA, a small RNA required for crRNA biogenesis) and a minimal CRISPR array optimized for one-step cloning of crRNA sequences, into the staphylococcal vector pC194, generating pDB114. This plasmid was programmed to target the aph-3 kanamycin resistance gene and the resulting construct, pDB114::aph, was transformed into *S. aureus* RN4220 and a kanamycin-resistant isogenic derivative, *S. aureus* RNK. Transformation efficiency of RNK cells was at least 2 orders of magnitude lower than RN4220 (FIG. 4), demonstrating Cas9-mediated killing of staphylococci.

Example 2

Figure 5:
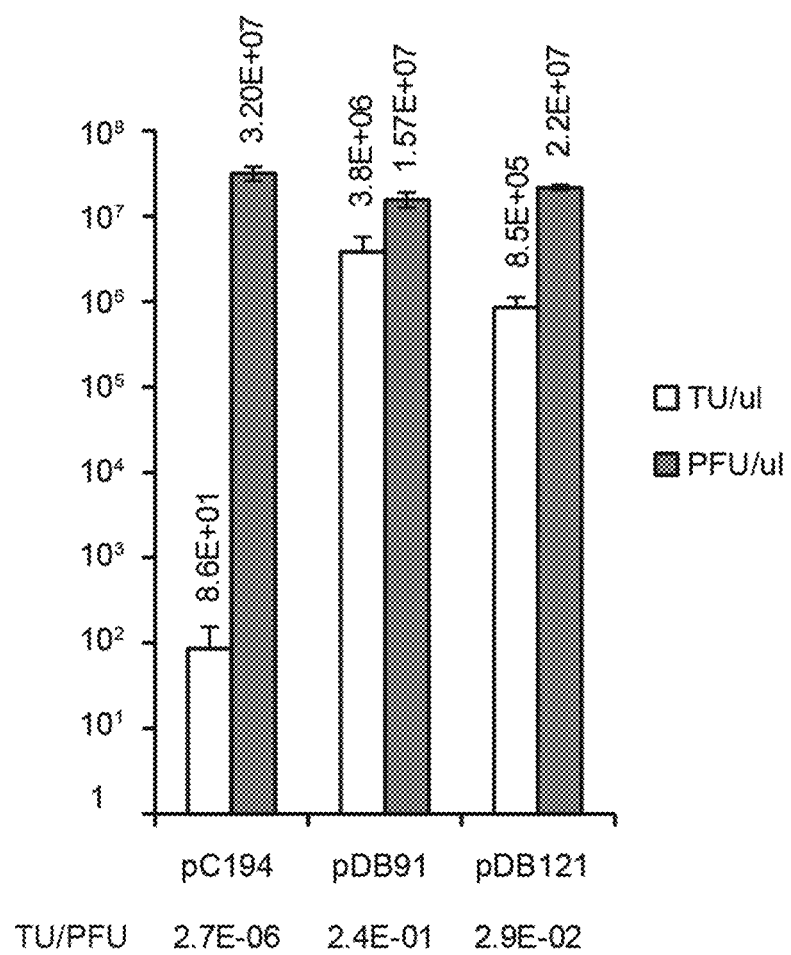
FIG. 5 shows an example of phagemid transduction efficiency. ΦNM1 lysates were prepared on RN4220 cells containing either pC194, pDB91 or pDB121. PFU/μl and TU/μl were measured as described in materials and methods (mean±s.d.).
Figure 6:
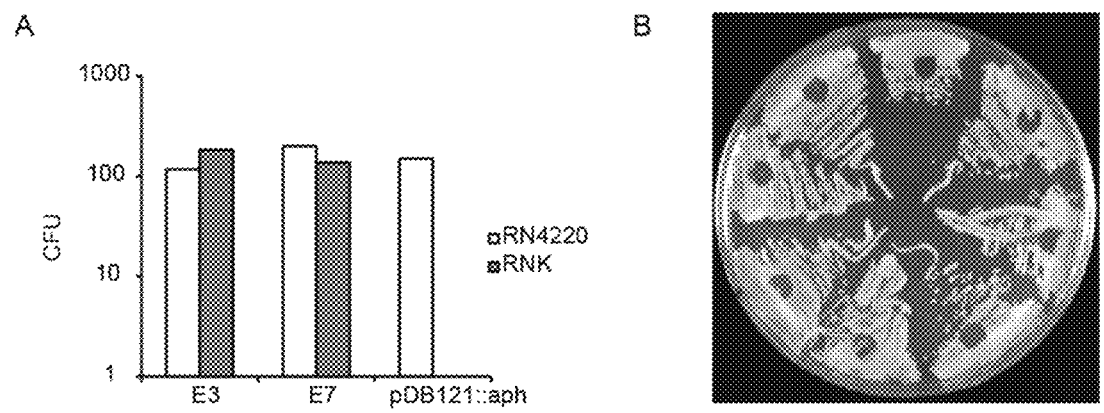
FIG. 6 shows and example of an analysis of survivor colonies. Eight colonies of RNK<sup>Φ</sup> that survived a treatment with pDB121::aph were re-streaked on TSA-chloramphenicol plates. Two chloramphenicol-resistant colonies were isolated, indicating that they carried the pDB121 plasmid (E3 and E7). (A) The plasmids from E3 and E7 were purified and retransformed in RN4220 or RNK electrocompetent cells and plated on TSA-chloramphenicol. While a control pDB 121::aph plasmid did not yield any colonies when transformed in RNK, plasmids prepared from E3 and E7 could be efficiently transformed, indicating that the CRISPR system was no longer functional. (B) In order to assess the integrity of the target, the survivor colonies were streaked on a HIA containing 5 mM $CaCl_2$ plate and a drop of pDB121::aph phagemid was added on top. Clearance indicates that the isolated colonies are still sensitive; hence the target is still intact.

In order to develop a phagemid system for *Staphylococcus aureus*, we cloned a ~2 kb fragment containing the rinA, terS and terL genes and packaging site from the staphylococcal ΦNM1 phage on plasmid pC194, obtaining pDB91. To assess the efficiency of packaging of pDB91 in ΦNM1 capsids, a transduction assay was performed. RN4220 cells containing pDB91 were infected with ΦNM1, and the lysate was used to transduce RN4220 cells previously lysogenized with ΦNM1, referred to as RN$^\Phi$. The lysogenic strain is resistant to superinfection which allows observation of phagemid transduction while negating the presence of wild-type phage in the lysate. We determined that a lysate with a titer of $1.6 \times 10^7$ plaque forming units (PFU)/μl contained $3.8 \times 10^6$ transfer units (TU)/μl, suggesting both a high efficiency of phagemid packaging (TU/PFU, 24%) as well as a high TU titer to treat a large bacterial population (FIG. 5). We cloned the CRISPR sequences of pDB114 and pDB144::aph into the pDB91 phagemid to obtain pDB121 and pDB121::aph, respectively. The proportion of phage particles that contained these phagemids was substantially lower (2.9% for pDB121, FIG. 5) than that for pDB91, most likely due to the larger size of pDB121 (10.3 kb vs. 5.3 kb), but remains high enough to perform delivery to a large number of cells. When spotted on a lawn of RNK$^\Phi$ cells, but not on a RN$^\Phi$ lawn, pDB121::aph elicited a strong growth inhibition (FIG. 1B). Conversely, the non-targeting pDB121 phagemid did not produce any inhibition of neither strain. In order to quantify the observed killing, infection experiments were performed at different multiplicity of infection (MOI). Here, we define the MOI as the number of TU per recipient cell. In targeting conditions cell killing is observed when the MOI becomes greater than one, while non-targeted cells remain unaffected (FIG. 1C). At an MOI of 20, the survival rate is of $1.1 \times 10^{-4}$. In order to investigate the nature of the survivor cells, colonies recovered after treatment were re-streaked on chloramphenicol plates, the resistance marker associated with the pDB121 phagemids. We found that ⅝ colonies were still sensitive to chloramphenicol, suggesting that they either lost the phagemid or did not receive it in the first place. A Poisson distribution with a mean of 20 gives a probability of a cell receiving no phagemid of only $1.5 \times 10^{-9}$, which is substantially lower than the survival rate observed. This either suggests that the injection of the phagemid in the recipient cells is not completely random, i.e. some cells are more likely to receive phagemids than others, or that the phagemids can be lost at a low rate. The remaining ⅔ chloramphenicol-resistant colonies were further analyzed to determine whether the aph-3 target and/or the CRISPR system were still intact. We found that they contained plasmids incapable of CRISPR targeting (FIG. 6A). None of the cells (⅝) able to escape phagemid treatment contained target mutations (FIG. 6B), indicating that such mutations happen at a frequency lower than 1 in $1.3 \times 10^5$ cells.

Example 3

Following treatment with conventional antibiotics that eradicate most members of a bacterial community, the rise and propagation of resistance is fueled by the lack of competitors in the treated environment. As shown above, sequence-specific killing is not exempt from the generation of cells that escape treatment, however this strategy has the benefit of killing only a subpopulation, leaving other members of the bacterial community and even of the same species to colonize the niche and limit the propagation of resistant organisms. To demonstrate this effect, we performed a treatment of RNK$^\Phi$ in which the pCN57 GFP reporter plasmid was transformed, either alone or in a co-culture with RN$^\Phi$. In both cases, the treatment effectively kills the targeted population, as evidenced by an interrupted increase of OD in the monoculture and GFP signal in the mixed culture respectively (FIG. 1D). After 7 hours, RNK$^\Phi$ cells that survived the treatment resume growth in the mono-culture whereas the fluorescence signal in the co-culture remains very low. This difference is most likely a consequence of the growth of the non-targeted RN$^\Phi$ cells, which out-competes the targeted RNK$^\Phi$ escaper cells for the medium nutrients, leaving them no opportunity to grow.

Example 4

Figure 2:
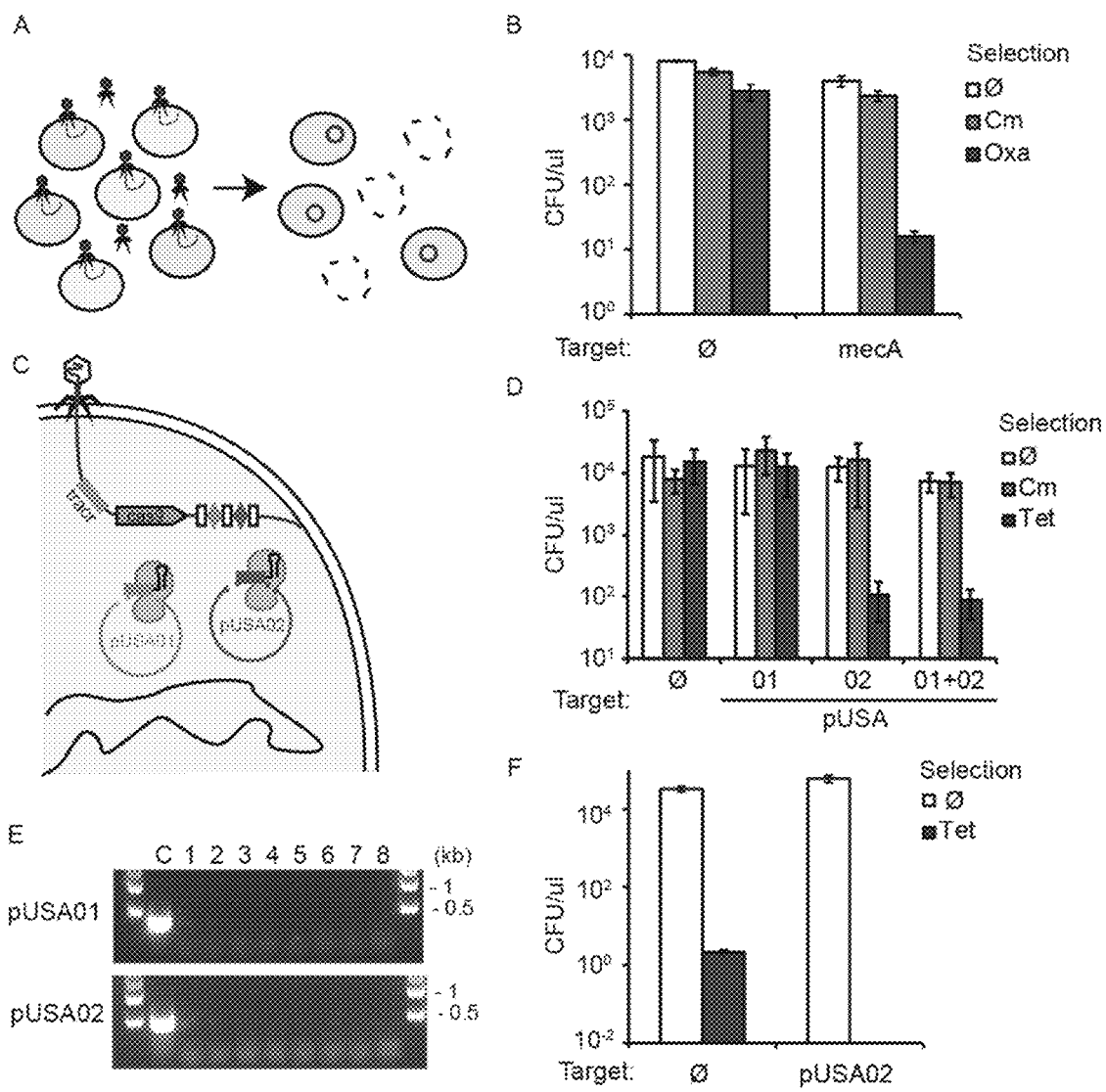
FIG. 2 shows an example of targeting of antibiotic resistance genes and plasmids in a MRSA strain. (A) Treatment of a mixed population results in killing of the targeted USA300 MRSA strain and delivery of an immunizing phagemid in the rest of the population. (B) pDB121::mecA specifically kills USA300<sup>Φ</sup> in a mixed population. Exponentially growing USA300<sup>Φ</sup> and RN<sup>Φ</sup> cells were mixed 1:1 and treated with pDB121 at an MOI of ~5. Cells were plated either on a non-selective medium, on chloramphenicol-containing medium to measure the proportion of cells receiving the phagemid treatment, or on oxacilin-containing medium to measure the proportion of USA300<sup>Φ</sup> cells in the population (mean±s.d.). (C) The CRISPR array can be programmed to target the pUSA01 and pUSA02 plasmids simultaneously. (D) USA300<sup>Φ</sup> was treated with pDB121 lysates targeting each plasmid individually or in combination. Cells were plated either on a non-selective medium, on chloramphenicol-containing medium to measure the proportion of cells receiving the phagemid treatment, or on tetracycline-containing medium to measure the proportion of cells being cured from pUSA02 (mean±s.d.). (E) Plasmid curing is confirmed by the lack of PCR amplification with plasmid specific oligonucleotides in 8 independent clones treated with the double targeting construct. (F) A population of RN<sup>Φ</sup> cells was immunized against plasmid horizontal transfer by treatment with the pUSA02-targeting pDB121 phagemid. 30 min after treatment, the population is transduced with a ΦNM1 stock grown on USA300. Cells are plated either without selection or on tetracycline to measure transduction efficiency of the pUSA02 plasmid (mean±s.d.).
Figure 7:
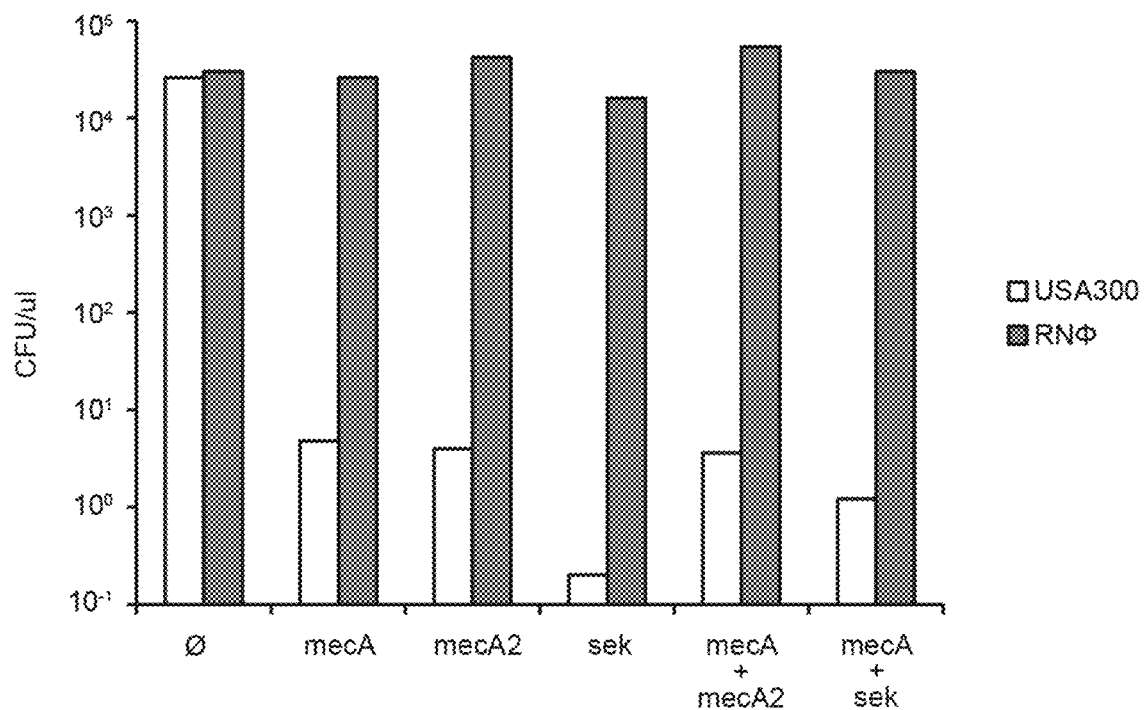
FIG. 7 shows an example of killing with multiple crRNA guides. Lysates of the pDB121 phagemid targeting carrying mecA, mecA2 or sek either alone or in combination were used to infect USA300 or RNK<sup>Φ</sup> cells with a MOI of ~10. Cells were plated on non-selective TSA plates.

We sought to use the sequence-specific killing strategy to eradicate MRSA strains from a mixed population of bacteria (FIG. 2A) and therefore we produced a phagemid targeting the methicillin resistance gene mecA, pDB121::mecA. This phagemid was used to treat the clinical isolate *S. aureus* USA300$^\Phi$ in a mixed culture with RN$^\Phi$ cells (both ΦNM1 lysogens). Exponentially growing USA300$^Φ$ and RN$^Φ$ cells were mixed 1:1 and treated with pDB121::mecA at an MOI of ~5. Cells were plated either to a non-selective medium, oxacillin-containing medium to measure the proportion of USA300$^Φ$ cells in the population, or on chloramphenicol-containing medium to measure the proportion of cells receiving the phagemid treatment (FIG. 2B). The proportion of USA300$^Φ$ dropped from 50% before treatment to 0.4% after treatment, while no significant drop could be observed in the control experiment using the non-targeting pDB121 phagemid. An advantage of using Cas9-mediated killing is the possibility of programming the nuclease with two or more crRNA guides in order to target different chromosomal sequences and limit the rise of resistant clones that escape phagemid treatment through the generation of target mutations. We achieved this by expanding the CRISPR array carried by the phagemid to produce a second crRNA targeting either the superantigen enterotoxin sek gene, or another region of the mecA gene. Both of these phagemids were shown to kill USA300$^Φ$ but not RN$^Φ$ (FIG. 7), and all survivor colonies isolated lacked target mutations (not shown). Consistently with the results we did not observed an additive effect in the killing efficiency of the multiple targeting phagemids, as survivor colonies either do not receive the phagemid or receive a defective CRISPR system.

Example 5

Plasmids are a predominant source of antibiotic resistance and virulence genes in pathogenic bacteria. The USA300 strain carries three of such plasmids, pUSA01-3, with the pUSA02 plasmid conferring tetracycline resistance to this strain. We designed phagemids that target pUSA01, pUSA02 or both (pUSA03 is unstable, data not shown) and tested them for their ability to cure this plasmids from the population (FIG. 2C). In all cases, treating USA300$^Φ$ with the phagemid preparation did not result in any cell death (FIG. 2D, CFU counts without selection similar to the non-targeting control). However, out of 8 colonies recovered for each experiment all had lost the targeted plasmid(s) (FIG. 2E). Loss of pUSA02 could be confirmed by the loss of tetracycline resistance in the treated cells (FIG. 2D). This demonstrates that delivery of the sequence-specific Cas9 nuclease dramatically reduce the plasmid content in a bacterial population, without killing the hosts. Many of these virulence plasmids are able to transfer horizontally and spread antibiotic resistance. We showed that pneumococci engineered to harbor a chromosomal type II CRISPR system programmed to target antibiotic resistance and virulence genes were prevented from acquiring these genes both in vitro and in vivo in a mouse model of pneumococcal infection. In this Example we tested whether phagemid treatment could be used to immunize naïve staphylococci against pUSA02 transfer. An exponentially growing culture of RN$^Φ$ cells was treated with the phagemid targeting the pUSA02 plasmid or the non-targeting control. After 30 minutes, the cells were infected with a ΦNM1 lysate grown on USA300 cells with the ability to transduce pUSA02. Transduction efficiency was measured by selecting for tetracycline resistance. While pUSA02 could readily be transferred to cells treated with the control phagemid, no tetracycline resistant colonies could be recovered with cells treated with the targeting phagemid (FIG. 2F), showing an efficient immunization against plasmid transfer.

Example 6

Figure 3:
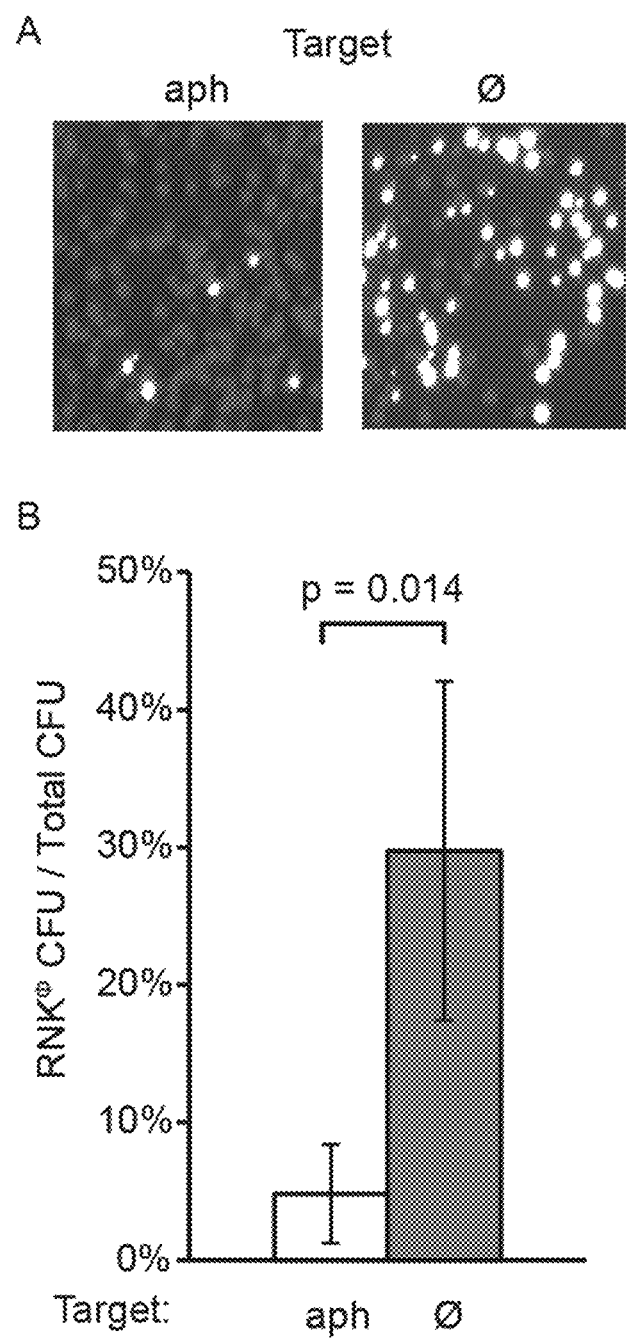
FIG. 3 shows an example of sequence specific killing of kanamycin resistant *S. aureus* in a mouse skin colonization model. Mice skin was colonized with a 1:1 mixture of $10^5$ RN<sup>Φ</sup> and RNK<sup>Φ</sup> cells carrying the pCN57 GFP reporter plasmid, followed by treatment at 1 hr with either pDB121::aph or a non-targeting control phagemid. After 24 hr the skin from the treated area was excised, homogenized and the cells plated on mannitol salt agar (A) Pictures of two representative plates in the GFP channel. (B) The proportion of RNK<sup>Φ</sup> cells in the population was measured as the proportion of green fluorescent colonies on the plates (mean±s.d.). The p-value of a two tailed student test not assuming equal variance is reported (n=5).

In order to demonstrate that phagemid treatment can be used to selectively kill staphylococci in vivo, we tested it in a mouse skin colonization model. The backs of CD1 mice were shaved and treated with depilatory cream to expose the skin. An area on the back was colonized with $10^5$ cells of a 1:1 mixture of RN$^Φ$ and RNK$^Φ$ bacteria, the latter harboring the pCN57 plasmid to facilitate detection of targeted cells by measuring green fluorescence. Following colonization, infected areas were treated with pDB121::aph or pDB121 and after 24 hr the treated skin was dissected and homogenized to enumerate staphylococci. The proportion of RNK$^Φ$ cells was measured as the ratio of GFP colonies in the population (FIG. 3A). After treatment the proportion of RNK$^Φ$ cells dropped from 50% to 4.8% and plating the cells on chloramphenicol showed that the phagemid was delivered to 89% of the cells (FIG. 3B). Unexpectedly, a smaller drop was also observed for mice treated with the control phagemid, possibly due to a fitness disadvantage of RNK$^Φ$/pCN57 cells when growing on the mouse skin. Thus, in this and the foregoing Examples, we demonstrate the use of programmable Cas9 nuclease activity as a sequence-specific antimicrobial and as a tool to manipulate heterogeneous bacterial populations. Besides the aspect of selective killing, provided with a suitable delivery system, the built-in multiplex feature of CRISPR-Cas systems could be exploited to target several different species at the same time and/or several sequences of the same bacterium to prevent the rise of resistant mutants. This approach can also be used to cure plasmids and other mobile genetic elements from a population without killing the host. Moreover, based on the present disclosure, the technology is easily adapted to repress the expression of antibiotic resistance, virulence and other genes of interest without causing the death of the host using dCas9, the nuclease-defective version of Cas9, as demonstrated herein in Example 7. These unique features create opportunities for the application of this technology in many medical, environmental and industrial settings.

Example 7

Figure 8:
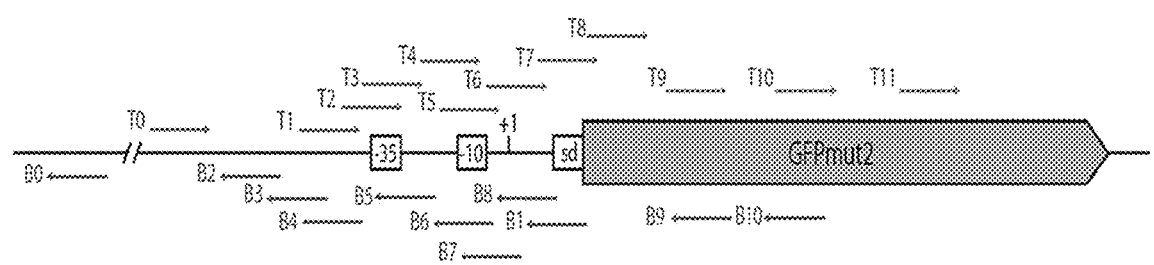
FIG. 8 demonstrates shows transcriptional repression using a modified Cas enzyme. Panel A) provides an illustrative representation of a gfpmut2 reporter gene showing positions that were targeted by the Cas9 D10A-H840 double mutant for repression of GFP expression. Panel B) shows repression at positions targeting the top-strand, while Panel C) shows targeting of the bottom-strand.
Figure 8:
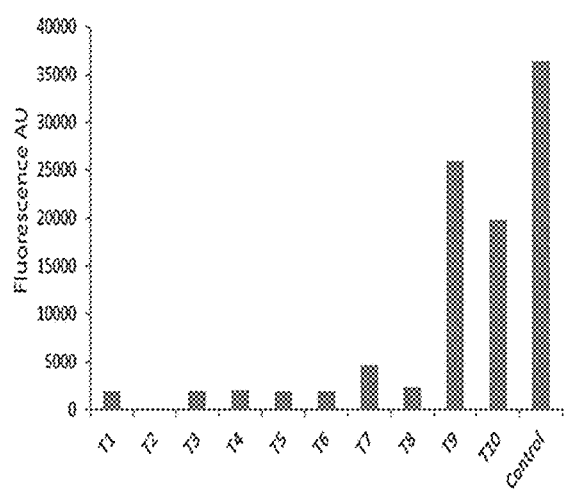
Figure 8:
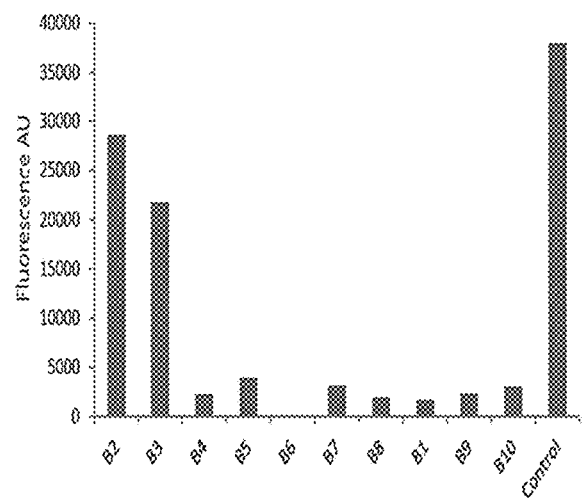

Double stranded cleavage of the target by Cas9 is achieved through the action of a RuvC domain on one strand and HNH domain on the other strand. We demonstrated that D10A and a H840A mutation in these respective domains abolish cleavage. In this Example we used the D10A-H840 double mutant, referred here as Cas9, to direct transcriptional repression. Cas9 was direct to bind various position in the promoter and gene of a GFP reporter. See FIG. 8, where panel (b) shows repression at positions targeting the top-strand, and panel (c) shows targeting of the bottom-strand.

Example 8

The Example provides a description of the materials and methods used to obtain the results described in the foregoing Examples.

Strains and culture conditions. *S. aureus* strain RN4220 was grown at 37 C in TSB, when appropriate, with the following antibiotics: kanamycin (Kan, 25 µg/ml), chloramphenicol (Cm, 10 µg/ml) and tetracycline (Tet, 5 µg/ml). *S. aureus* USA300 was provided by the Fischetti lab. Phage ΦNM1 was isolated from the *S. aureus* Newman strain. The supernatant of an overnight culture was used to infect RN4220 in a top-agar layer. Single plaques were isolated and passaged 3 times to ensure purity. ΦNM1 lysogens of RN4220 (RN$^Φ$) and USA300 (USA$^Φ$) were isolated by re-streaking cells from the middle of a turbid plaque twice. Chromosomal integration of ΦNM1 was checked by both PCR and by ensuring resistance to ΦNM1 superinfection. A kanamycin resistance gene was introduced in RN4220 by using a derivative of the pCL55-itet integrative vector where the chloramphenicol resistance gene was replaced with the aphA-3 kanamycin resistance gene to produce pKL55-itet. Briefly, aphA-3 was amplified from strain crR6 using primers L484/L485 and pCL55-itet was amplified with primers L482/L483, followed by digestion with XhoI and ligation. Integration in the RN4220 chromosome was achieved by transformation in electrocompetent cells and selection on TSA+Kan.

Plasmid construction. To assemble the pDB91 phagemid, the rinA-terS-terL region of ΦNM1 was amplified with oligos B234/B235, and pC194 with oligos B233/B127. PCR products were digested with KpnI and SphI followed by ligation and transformation in RN4220 competent cells. The pDB114 plasmid was constructed in two steps. First the full MIGAS S. pyogenes CRISPR02 system was cloned on pC194 by amplifying S. pyogenes genomic DNA with oligos L362/W278 and pC194 with oligos W270/W282, followed by digestion with BglII and BssSI and ligation, giving pWJ40. The pWJ40 plasmid was then amplified with oligos B334/L410 and the BsaI CRISPR array from pCas9 with oligos L409/B333, followed by Gibson assembly. To construct pDB121, pDB114 was amplified with oligos B351/W278 and pDB91 with oligos L316/L318, followed by Gibson assembly of the two fragments. Spacers were cloned by digestion with BsaI, and ligation of annealed oligonucleotides designed as follow: 5'-aaac+(target sequence)+g-3' and 5'-aaaac+(reverse complement of the target sequence)-3', where the target sequence is 30 nt and is followed by a functional PAM (NGG). Alternatively, two spacers were cloned in a single reaction in the BsaI digested pDB121 vector. Two pairs of oligonucleotides were annealed and ligated with the vector. The pair carrying the first spacer was designed as follow: 5'-aaac+(target sequence)+GTTT-TAGAGCTATG-3' (SEQ ID NO:35) and 5'-AACAGCAT-AGCTCTAAAAC+(reverse complement of the target sequence)-3' (SEQ ID NO:36), and the pair carrying the second spacer as follow: 5'-CTGTTTTGAATGGTCC-CAAAAC+(target sequence)+g-3' (SEQ ID NO:37) and 5'-aaaac+(reverse complement of the target sequence)+GTTTTGGGACCATTCAA-3'(SEQ ID NO:38). A list of all spacers tested in this study is provided in Table 1, and a list of oligonucleotides in Table 2.

Phage and phagemid production. Phage and phagemid stocks were produced by growing cells from an overnight culture diluted 1:50 in TSB+Cm+CaCl2 5 mM until an OD600 of 0.6. The cultures were then inoculated with 10 μl of a concentrated ΦNM1 phage stock and incubated for 3 H. Cell debris was eliminated by centrifugation and filtering of the supernatant through 0.45 um filters. Phage titers were determined by serial dilution and spotting on a top-agar layer of RN4220 cells on HIA plates supplemented with 5 mM CaCl2. To determine the transducing titer, serial dilutions of the phage stock were produced and used to infect a culture of RN$^Φ$ cells grown to OD~1. After 1 H of incubation at 37 C, cells were plated on TSA+Cm, and transducing units (TU) were measured from the number of CFU obtained.

Killing and plasmid curing assays. Phage stocks were produced on RN4220 cells carrying a phagemid with the desired CRISPR spacer. Recipient cells were grown in TSB to an OD600 of 0.6, diluted 10× in TSB+5 mM CaCl2 and 100 μl of the culture was mixed with 100 μl of the appropriate phage stock dilution. After 1 H of incubation, cells were plated on TSA. Survival rates were measured as the ratio of CFUs obtained with treatment over CFUs obtained without treatment. When appropriate, cells were also plated on TSA+Cm to measure phagemid transduction efficiency, TSA+Tet to measure pUSA02 curing, and TSA+Oxa to measure the proportion of MRSA cells in the population.

Immunization assay. RN$^Φ$ cells were diluted 1:100 in TSB and grown to OD600 of 0.2. Phagemid was added to an MOI of 10, and cells were incubated 30 min to allow for establishment of the CRISPR system. The pUSA02 plasmid was transduced by infecting with a phiNM1 stock grown on USA300 cells. Cells were plated on TSB, TSB+Cm or TSB+Tet to measure transduction efficiency.

Growth curves and fluorescence measurements. Growth curves and GFP fluorescence were measured in a Tecan microplate reader. Cultures were started by diluting a ON culture 1:100 in 200 μl of TSB. Phagemid was added to an MOI of ~10 after 80 min of growth.

Mouse skin colonization. The Rockefeller University's Institutional Animal Care and Use Committee approved all in vivo protocols. All experiments were conducted at The Rockefeller University's Animal housing facility, an AAALAC accredited research facility with all efforts to minimalize suffering. An adapted approach from Kugelberg et al. and Pastagia et al. was used to induce topical skin colonization with S. aureus on 6- to 8-week-old female CD1 mice (Charles River Laboratories, Wilmington, MA). Briefly, mice were anesthetized by intraperitoneal injection of ketamine (1.5 mg/animal; Fort Dodge Animal Health, Fort Dodge, IA) and xylazine (0.3 mg/animal; Miles Inc., Shawnee Mission, KS). A 2 cm$^2$ area of the dorsum of each mouse was shaved with an electric razor; Nair depilatory cream was then applied to the shaved area for one minute and wiped away with 70% ethanol pads. The area was then tape stripped, with autoclave tape, approximately 10 times in succession, using a fresh piece of tape each time to irritate and remove the upper layers of the epidermis. The mice were topically colonized with a 2 μl mixture of cultures of S. aureus RN$^Φ$ and RNK$^Φ$/pCN57 containing 1×10$^5$ cells in logarithmic growth phases in PBS. Animals were then immobilized under isoflurane anesthesia. After 1 H, 10 μl of concentrated phagemid lysate containing 2×10$^7$ TU/μl was applied on the infected skin area. To obtain this concentration, crude lysates were concentrated using 100 kD Amicon Ultra centrifugal filters and washed once with PBS. After 24 H, tissue from the infected skin area was excised and homogenized in 0.5 ml of PBS using the Stomacher 80. Bacterial dilutions were plated on mannitol salt agar (an S. aureus-selective medium) and TSA+Cm.

TABLE 1

Spacers used in this disclosure.

| Target | Spacer sequence (5'-3') |
|---|---|
| aph | TCATGAGTGAGGCCGATGGCGTCCTTTGCT (SEQ ID NO: 1) |
| mecA | TTTTGAGTTGAACCTGGTGAAGTTGTAATC (SEQ ID NO: 2) |
| mecA2 | CATTTTCTTTGCTAGAGTAGCACTCGAATT (SEQ ID NO: 3) |
| sek | GATTATCAATTCCTATATCACCTTGAGCGC (SEQ ID NO: 4) |
| pUSA01 | CTTATGTAACTTCAAATAGCCTTCATCAGT (SEQ ID NO: 5) |
| pUSA02 | AGGAGTAGTATTAAAATGATTTGCAATATC (SEQ ID NO: 6) |

TABLE 2

Oligonucleotides used in this disclosure.

| Name | Sequence (5'-3') |
|---|---|
| B234 | TTTAGGTACCAAGAGCGAGAGATAGAGATATTAAG (SEQ ID NO: 7) |
| B235 | TTTAGCATGCCTATAATCCTAGAGATTTTATTGTGT (SEQ ID NO: 8) |
| B127 | AAAAGCATGCAAATATGAGCCAAATAAATATATTC (SEQ ID NO: 9) |
| B233 | TACTGGTACCTTTAAAAGCTTCTGTAGGTTTTTAG (SEQ ID NO: 10) |
| L362 | aaactcgtgGATTCTGTGATTTGGATCCTTCC (SEQ ID NO: 11) |
| W278 | aaaaagatctTATGACTGTTATGTGGTTATCG (SEQ ID NO: 12) |
| W270 | aaaaagatctTGCATAATTCACGCTGACCTC (SEQ ID NO: 13) |
| W282 | aaaacacgagCGTTTGTTGAACTAATGGGTGC (SEQ ID NO: 14) |
| L410 | CTTCACTTGGAACGTTATCCGATTTACCACG (SEQ ID NO: 15) |
| L409 | CGTGGTAAATCGGATAACGTTCCAAGTGAAG (SEQ ID NO: 16) |
| B333 | CTTTATCCAATTTTCGTTTGAACTCAACAAGTCTCAGTGTGCTG (SEQ ID NO: 17) |
| B334 | ACACTGAGACTTGTTGAGTTCAAACGAAAATTGGATAAAGTGGG (SEQ ID NO: 18) |
| L316 | TTAAGGGTTCTTCTCAACGCAC (SEQ ID NO: 19) |
| L318 | TTAAAAGTTATTGTGATGACGACG (SEQ ID NO: 20) |
| B351 | ATCGTTTATCGTCGTCATCACAATAACTTTTAAAGATCTTGCATAATTCACGCTGAC (B351 is SEQ ID NO: 21) |
| L482 | aaaCTCGAGCTGAGAGTGCACCATATGCGG (SEQ ID NO: 22) |
| L483 | aaaCTCGAGCTTAATAGCTCACGCTATGCCG (SEQ ID NO: 23) |
| L484 | aaaCTCGAGCGCGCAAGCTGGGGATCCG (SEQ ID NO: 24) |
| L485 | aaaCTCGAGTAGGTACTAAAACAATTCATCCAG (SEQ ID NO: 25) |
| B628 | AGTGGGAAACAACGCCCATGGAG (SEQ ID NO: 26) |
| B629 | GTTGAACGCATAAATCCAACAAG (SEQ ID NO: 27) |
| B632 | AGTCACCTCAAGTAAAGAGGTAA (SEQ ID NO: 28) |
| B633 | TGAAGGACCTAACCCTTCACCTA (SEQ ID NO: 29) |

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A method for selectively modifying a mixed population of bacteria, wherein the mixed population of bacteria comprises at least a first and a second bacterial species, comprising:

(a) contacting the mixed population of bacteria with packaged, recombinant phagemids that are packaged in phage capsids, wherein the packaged phagemids comprise a clustered regularly interspaced short palindromic repeats (CRISPR) system comprising i) a type II CRISPR-associated enzyme and ii) two or more crRNA guides that target different chromosomal sequences in bacterial cells of the second bacterial species and, (b) producing the crRNA guides in the bacterial cells of the second bacterial species, wherein the crRNA guides comprise i) a first crRNA guide complementary to a first target chromosomal sequence in the bacterial cells of the second bacterial species and ii) a second crRNA guide complementary to a second target chromosomal sequence in the bacterial cells of the second bacterial species, wherein the second target chromosomal sequence is different from the first target chromosomal sequence; and wherein:

1) the first target chromosomal sequence is comprised by a first antibiotic resistance gene and the second target chromosomal sequence is comprised by a second antibiotic resistance gene, 2) the first target chromosomal sequence is comprised by an antibiotic resistance gene and the second target chromosomal sequence is comprised by a virulence gene, or 3) the first target chromosomal sequence is comprised by a first virulence gene and the second target chromosomal sequence is comprised by a second virulence gene;

wherein the expressed type II CRISPR-associated enzyme cleaves the first and second target chromosomal sequences at the target sites of the crRNA guides in the bacterial cells of the second bacterial species, wherein the first and second bacterial species are different and are selected from *Streptococcus, Staphylococcus, Clostridium, Bacillus, Salmonella, Helicobacter pylori, Neisseria gonorrhoeae, Neisseria meningitidis,* and *Escherichia coli*, and wherein the growth of the bacterial cells of the first bacterial species in the mixed population is not inhibited, and wherein at least 50% of the bacterial cells of the second bacterial species are killed.

2. The method of claim 1, wherein the mixed population of bacteria comprises *E. coli*.

3. The method of claim 1, wherein the mixed population of bacteria comprises *Streptococcus*.

4. The method of claim 1, wherein the mixed population of bacteria comprises *Staphylococcus*.

5. The method of claim 1, wherein the mixed population of bacteria comprises *Salmonella*.

6. The method of claim 1, wherein the mixed population of bacteria comprises *Clostridium*.

7. The method of claim 1, wherein the second bacterial species is *Staphylococcus*.

8. The method of claim 7, wherein the second bacterial species is *Staphylococcus aureus*.

9. The method of claim 8, wherein the second bacterial species is a methicillin-resistant *Staphylococcus aureus*.

10. The method of claim 9, wherein the first target chromosomal sequence is the mecA gene and the second target chromosomal sequence is the sek gene.

11. The method of claim 10, wherein the type II Cas is a Cas9.

12. The method of claim 11, wherein the type II Cas is a *Streptococcus* Cas9.

13. The method of claim 7, wherein the first bacterial species is selected from *Streptococcus, Clostridium, Bacillus, *Salmonella, Helicobacter pylori, Neisseria gonorrhoeae, Neisseria meningitidis*, and *Escherichia coli*.

14. The method of claim 13, wherein the first bacterial species is *Streptococcus*.

15. The method of claim 13, wherein the first bacterial species is *Clostridium*.

16. The method of claim 13, wherein the first bacterial species is *Bacillus*.

17. The method of claim 13, wherein the first bacterial species is *Salmonella*.

18. The method of claim 13, wherein the first bacterial species is *Helicobacter pylori*.

19. The method of claim 13, wherein the first bacterial species is *Neisseria gonorrhoeae*.

20. The method of claim 13, wherein the first bacterial species is *Neisseria meningitidis*.

21. The method of claim 13, wherein the first bacterial species is *Escherichia coli*.

22. The method of claim 1, wherein the type II Cas is a Cas9.

23. The method of claim 22, wherein the type II Cas is a *Streptococcus* Cas9.

24. The method of claim 23, wherein at least 99.9% of the bacterial cells of the second bacterial species are killed.

* * * * *

SEQUENCE LISTING

```
Sequence total quantity: 38
SEQ ID NO: 1           moltype = DNA  length = 30
FEATURE                Location/Qualifiers
source                 1..30
                       mol_type = other DNA
                       organism = Staphylococcus aureus
SEQUENCE: 1
tcatgagtga ggccgatggc gtcctttgct                                    30

SEQ ID NO: 2           moltype = DNA  length = 30
FEATURE                Location/Qualifiers
source                 1..30
                       mol_type = other DNA
                       organism = Staphylococcus aureus
SEQUENCE: 2
ttttgagttg aacctggtga agttgtaatc                                    30

SEQ ID NO: 3           moltype = DNA  length = 30
```

```
FEATURE              Location/Qualifiers
source               1..30
                     mol_type = other DNA
                     organism = Staphylococcus aureus
SEQUENCE: 3
cattttcttt gctagagtag cactcgaatt                                        30

SEQ ID NO: 4         moltype = DNA   length = 30
FEATURE              Location/Qualifiers
source               1..30
                     mol_type = other DNA
                     organism = Staphylococcus aureus
SEQUENCE: 4
gattatcaat tcctatatca ccttgagcgc                                        30

SEQ ID NO: 5         moltype = DNA   length = 30
FEATURE              Location/Qualifiers
source               1..30
                     mol_type = other DNA
                     organism = Staphylococcus aureus
SEQUENCE: 5
cttatgtaac ttcaaatagc cttcatcagt                                        30

SEQ ID NO: 6         moltype = DNA   length = 30
FEATURE              Location/Qualifiers
source               1..30
                     mol_type = other DNA
                     organism = Staphylococcus aureus
SEQUENCE: 6
aggagtagta ttaaaatgat ttgcaatatc                                        30

SEQ ID NO: 7         moltype = DNA   length = 35
FEATURE              Location/Qualifiers
misc_feature         1..35
                     note = Oligonucleotide
source               1..35
                     mol_type = other DNA
                     organism = synthetic construct
SEQUENCE: 7
tttaggtacc aagagcgaga gatagagata ttaag                                  35

SEQ ID NO: 8         moltype = DNA   length = 36
FEATURE              Location/Qualifiers
misc_feature         1..36
                     note = Oligonucleotide
source               1..36
                     mol_type = other DNA
                     organism = synthetic construct
SEQUENCE: 8
tttagcatgc ctataatcct agagatttta ttgtgt                                 36

SEQ ID NO: 9         moltype = DNA   length = 35
FEATURE              Location/Qualifiers
misc_feature         1..35
                     note = Oligonucleotide
source               1..35
                     mol_type = other DNA
                     organism = synthetic construct
SEQUENCE: 9
aaaagcatgc aaatatgagc caaataaata tattc                                  35

SEQ ID NO: 10        moltype = DNA   length = 35
FEATURE              Location/Qualifiers
misc_feature         1..35
                     note = Oligonucleotide
source               1..35
                     mol_type = other DNA
                     organism = synthetic construct
SEQUENCE: 10
tactggtacc tttaaaagct tctgtaggtt tttag                                  35

SEQ ID NO: 11        moltype = DNA   length = 32
FEATURE              Location/Qualifiers
misc_feature         1..32
                     note = Oligonucleotide
source               1..32
                     mol_type = other DNA
                     organism = synthetic construct
SEQUENCE: 11
```

```
aaactcgtgg attctgtgat ttggatccttt cc                                    32

SEQ ID NO: 12           moltype = DNA   length = 32
FEATURE                 Location/Qualifiers
misc_feature            1..32
                        note = Oligonucleotide
source                  1..32
                        mol_type = other DNA
                        organism = synthetic construct
SEQUENCE: 12
aaaaagatct tatgactgtt atgtggttat cg                                     32

SEQ ID NO: 13           moltype = DNA   length = 31
FEATURE                 Location/Qualifiers
misc_feature            1..31
                        note = Oligonucleotide
source                  1..31
                        mol_type = other DNA
                        organism = synthetic construct
SEQUENCE: 13
aaaaagatct tgcataattc acgctgacct c                                      31

SEQ ID NO: 14           moltype = DNA   length = 32
FEATURE                 Location/Qualifiers
misc_feature            1..32
                        note = Oligonucleotide
source                  1..32
                        mol_type = other DNA
                        organism = synthetic construct
SEQUENCE: 14
aaaacacgag cgtttgttga actaatgggt gc                                     32

SEQ ID NO: 15           moltype = DNA   length = 31
FEATURE                 Location/Qualifiers
misc_feature            1..31
                        note = Oligonucleotide
source                  1..31
                        mol_type = other DNA
                        organism = synthetic construct
SEQUENCE: 15
cttcacttgg aacgttatcc gatttaccac g                                      31

SEQ ID NO: 16           moltype = DNA   length = 31
FEATURE                 Location/Qualifiers
misc_feature            1..31
                        note = Oligonucleotide
source                  1..31
                        mol_type = other DNA
                        organism = synthetic construct
SEQUENCE: 16
cgtggtaaat cggataacgt tccaagtgaa g                                      31

SEQ ID NO: 17           moltype = DNA   length = 44
FEATURE                 Location/Qualifiers
misc_feature            1..44
                        note = Oligonucleotide
source                  1..44
                        mol_type = other DNA
                        organism = synthetic construct
SEQUENCE: 17
ctttatccaa ttttcgtttg aactcaacaa gtctcagtgt gctg                        44

SEQ ID NO: 18           moltype = DNA   length = 44
FEATURE                 Location/Qualifiers
misc_feature            1..44
                        note = Oligonucleotide
source                  1..44
                        mol_type = other DNA
                        organism = synthetic construct
SEQUENCE: 18
acactgagac ttgttgagtt caaacgaaaa ttggataaag tggg                        44

SEQ ID NO: 19           moltype = DNA   length = 22
FEATURE                 Location/Qualifiers
misc_feature            1..22
                        note = Oligonucleotide
source                  1..22
                        mol_type = other DNA
                        organism = synthetic construct
```

```
SEQUENCE: 19
ttaagggttc ttctcaacgc ac                                           22

SEQ ID NO: 20           moltype = DNA  length = 24
FEATURE                 Location/Qualifiers
misc_feature            1..24
                        note = Oligonucleotide
source                  1..24
                        mol_type = other DNA
                        organism = synthetic construct
SEQUENCE: 20
ttaaaagtta ttgtgatgac gacg                                         24

SEQ ID NO: 21           moltype = DNA  length = 57
FEATURE                 Location/Qualifiers
misc_feature            1..57
                        note = Oligonucleotide
source                  1..57
                        mol_type = other DNA
                        organism = synthetic construct
SEQUENCE: 21
atcgtttatc gtcgtcatca caataacttt taaagatctt gcataattca cgctgac     57

SEQ ID NO: 22           moltype = DNA  length = 30
FEATURE                 Location/Qualifiers
misc_feature            1..30
                        note = Oligonucleotide
source                  1..30
                        mol_type = other DNA
                        organism = synthetic construct
SEQUENCE: 22
aaactcgagc tgagagtgca ccatatgcgg                                   30

SEQ ID NO: 23           moltype = DNA  length = 31
FEATURE                 Location/Qualifiers
misc_feature            1..31
                        note = Oligonucleotide
source                  1..31
                        mol_type = other DNA
                        organism = synthetic construct
SEQUENCE: 23
aaactcgagc ttaatagctc acgctatgcc g                                 31

SEQ ID NO: 24           moltype = DNA  length = 28
FEATURE                 Location/Qualifiers
misc_feature            1..28
                        note = Oligonucleotide
source                  1..28
                        mol_type = other DNA
                        organism = synthetic construct
SEQUENCE: 24
aaactcgagc gcgcaagctg gggatccg                                     28

SEQ ID NO: 25           moltype = DNA  length = 33
FEATURE                 Location/Qualifiers
misc_feature            1..33
                        note = Oligonucleotide
source                  1..33
                        mol_type = other DNA
                        organism = synthetic construct
SEQUENCE: 25
aaactcgagt aggtactaaa acaattcatc cag                               33

SEQ ID NO: 26           moltype = DNA  length = 23
FEATURE                 Location/Qualifiers
misc_feature            1..23
                        note = Oligonucleotide
source                  1..23
                        mol_type = other DNA
                        organism = synthetic construct
SEQUENCE: 26
agtgggaaac aacgcccatg gag                                          23

SEQ ID NO: 27           moltype = DNA  length = 23
FEATURE                 Location/Qualifiers
misc_feature            1..23
                        note = Oligonucleotide
source                  1..23
                        mol_type = other DNA
```

```
                        organism = synthetic construct
SEQUENCE: 27
gttgaacgca taaatccaac aag                                               23

SEQ ID NO: 28           moltype = DNA   length = 23
FEATURE                 Location/Qualifiers
misc_feature            1..23
                        note = Oligonucleotide
source                  1..23
                        mol_type = other DNA
                        organism = synthetic construct
SEQUENCE: 28
agtcacctca agtaaagagg taa                                               23

SEQ ID NO: 29           moltype = DNA   length = 23
FEATURE                 Location/Qualifiers
misc_feature            1..23
                        note = Oligonucleotide
source                  1..23
                        mol_type = other DNA
                        organism = synthetic construct
SEQUENCE: 29
tgaaggacct aacccttcac cta                                               23

SEQ ID NO: 30           moltype = DNA   length = 171
FEATURE                 Location/Qualifiers
source                  1..171
                        mol_type = other DNA
                        organism = Streptococcus pyogenes
SEQUENCE: 30
agtattaagt attgttttat ggctgataaa tttctttgaa tttctccttg attatttgtt        60
ataaaagtta taaataatc ttgttggaac cattcaaaac agcatagcaa gttaaaataa       120
ggctagtccg ttatcaactt gaaaaagtgg caccgagtcg gtgcttttt t                 171

SEQ ID NO: 31           moltype = DNA   length = 89
FEATURE                 Location/Qualifiers
source                  1..89
                        mol_type = other DNA
                        organism = Streptococcus pyogenes
SEQUENCE: 31
gttggaacca ttcaaaacag catagcaagt taaataagg ctagtccgtt atcaacttga         60
aaaagtggca ccgagtcggt gcttttttt                                         89

SEQ ID NO: 32           moltype = DNA   length = 75
FEATURE                 Location/Qualifiers
source                  1..75
                        mol_type = other DNA
                        organism = Streptococcus pyogenes
SEQUENCE: 32
aaacagcata gcaagttaaa ataaggctag tccgttatca acttgaaaaa gtggcaccga        60
gtcggtgctt ttttt                                                        75

SEQ ID NO: 33           moltype = DNA   length = 22
FEATURE                 Location/Qualifiers
misc_feature            1..22
                        note = phagemid
source                  1..22
                        mol_type = other DNA
                        organism = synthetic construct
SEQUENCE: 33
gttttagagc tatgctgttt tg                                                22

SEQ ID NO: 34           moltype = DNA   length = 36
FEATURE                 Location/Qualifiers
misc_feature            1..36
                        note = Phagemid
source                  1..36
                        mol_type = other DNA
                        organism = synthetic construct
SEQUENCE: 34
gttttagagc tatgctgttt tgaatggtcc caaaac                                 36

SEQ ID NO: 35           moltype = DNA   length = 13
FEATURE                 Location/Qualifiers
misc_feature            1..13
                        note = Oligonucleotide
source                  1..13
                        mol_type = other DNA
                        organism = synthetic construct
```

```
SEQUENCE: 35
ttttagagct atg                                                                    13

SEQ ID NO: 36          moltype = DNA  length = 19
FEATURE                Location/Qualifiers
misc_feature           1..19
                       note = Oligonucleotide
source                 1..19
                       mol_type = other DNA
                       organism = synthetic construct
SEQUENCE: 36
aacagcatag ctctaaaac                                                              19

SEQ ID NO: 37          moltype = DNA  length = 22
FEATURE                Location/Qualifiers
misc_feature           1..22
                       note = Oligonucleotide
source                 1..22
                       mol_type = other DNA
                       organism = synthetic construct
SEQUENCE: 37
ctgttttgaa tggtcccaaa ac                                                          22

SEQ ID NO: 38          moltype = DNA  length = 17
FEATURE                Location/Qualifiers
misc_feature           1..17
                       note = Oligonucleotide
source                 1..17
                       mol_type = other DNA
                       organism = synthetic construct
SEQUENCE: 38
gttttgggac cattcaa                                                                17
```